(12) United States Patent
Wischik et al.

(10) Patent No.: US 8,263,589 B2
(45) Date of Patent: Sep. 11, 2012

(54) INHIBITORS OF PROTEIN AGGREGATION

(75) Inventors: Claude Michel Wischik, Aberdeen (GB); Janet Elizabeth Rickard, Aberdeen (GB); Charles Robert Harrington, Aberdeen (GB); David Horsley, Ellon (GB)

(73) Assignee: Wista Laboratories Ltd., Singapore (SG)

( * ) Notice: Subject to any disclaimer, the term of this patent is extended or adjusted under 35 U.S.C. 154(b) by 560 days.

(21) Appl. No.: 12/294,605

(22) PCT Filed: Mar. 28, 2007

(86) PCT No.: PCT/GB2007/001105
§ 371 (c)(1),
(2), (4) Date: Nov. 11, 2008

(87) PCT Pub. No.: WO2007/110629
PCT Pub. Date: Oct. 4, 2007

(65) Prior Publication Data
US 2009/0209526 A1 Aug. 20, 2009

Related U.S. Application Data

(60) Provisional application No. 60/786,700, filed on Mar. 29, 2006.

(51) Int. Cl.
*A61K 31/54* (2006.01)
*C07D 279/36* (2006.01)
(52) U.S. Cl. ...................... 514/224.8; 544/31
(58) Field of Classification Search ............... 514/224.8; 544/31
See application file for complete search history.

(56) References Cited

U.S. PATENT DOCUMENTS

| 5,827,644 | A | 10/1998 | Floyd et al. |
| 2,928,767 | A1 | 5/2008 | Gulesich et al. |
| 2003/0217370 | A1 | 11/2003 | Giasson |

FOREIGN PATENT DOCUMENTS

| EP | 1067386 | | 10/2001 |
| EP | 1739425 | A | 1/2007 |
| FR | 2 788 436 | | 7/2000 |
| WO | WO 96/04915 | | 2/1996 |
| WO | WO 96/05837 | | 2/1996 |
| WO | WO 02/03972 | A | 1/2002 |
| WO | WO 02/04025 | | 1/2002 |
| WO | WO 02/04025 | A | 1/2002 |
| WO | WO 02/055720 | | 7/2002 |
| WO | WO 02/055720 | A2 | 7/2002 |
| WO | WO 02/059150 | | 8/2002 |
| WO | WO 02/075318 | | 9/2002 |
| WO | WO 03/007933 | | 1/2003 |
| WO | WO 2005/030676 | | 4/2005 |
| WO | WO 2005/095958 | A | 10/2005 |
| WO | WO 2006/032879 | | 3/2006 |
| WO | WO 2006/122546 | | 11/2006 |
| WO | WO 2007/110627 | | 10/2007 |

OTHER PUBLICATIONS

Intelihealth, "Parkinson's disease," online, accessed Sep. 22, 2009, http://www.intelihealth.com/IH/ihtIH?d=dmtHealthAZ&c=201957.*
Olanow CW. "A rational approach to the treatment of early Parkinson's disease." Parkinsonism & Related Diseases. Dec. 1999; 5(4): 217-220.*
Stedman's Medical Dictionary, 27th ed., Lippincott, Eilliams & Wilkins, Baltimore, 2000.*
International Search Report for PCT/GB2007/001105 dated Jul. 13, 2007. (5 pgs.).
Masuda, et al., Small Molecule Inhibitors of Alpha-Synuclein Filament Assembly, *Biochemistry*, vol. 45, No. 19, May 2006, pp. 6085-6094.
Zhang, et al., "Methylene Blue Prevents Neurodegeneration Caused by Rotenone in the Retina", *Neurotoxicity Research*, vol. 9, No. 1, 2006, pp. 47-57.
U.S. Appl. No. 10/107,181, filed Mar. 28, 2002, Wischik.
U.S. Appl. No. 11/175,153, filed Jul. 7, 2005, Wischik.
U.S. Appl. No. 11/391,675, filed Mar. 29, 2006, Wischik.
U.S. Appl. No. 60/945,006, filed Jun. 19, 2007, Wischik.
U.S. Appl. No. 60/996,177, filed Nov. 5, 2007, Wischik.
U.S. Appl. No. 61/077,281, filed Jul. 1, 2008, Wischik.
Callaway, N.L. et al, "Methylene blue restores spatial memory retention impaired by an inhibitor of cytochrome oxidase in rats" Neuroscience Letters 332, (2002), pp. 83-86.
Chemistry and Biology "Targeting α-Synuclein in Parkinson's Disease" pp. 1476-1478, 2004.
Epstein, J.B. et al, "The utility of toluidine blue application as a diagnostic aid in patients previously treated for upper oropharyngeal carcinoma" Oral medicine, (1997), pp. 537-547, vol. 83, No. 5.
Grover, A., et al., "5' splice site mutations in tau associated with the inherited dementia FTDP-17 affect a stem-loop structure that regulates alternative splicing of Exon 10*" The Journal of Biological Chemistry (1999), pp. 15134-15143, vol. 274, May 21 issue No. 21.
Harada, A., et al., "Altered microtubule organization in small-calibre axons of mice lacking tau protein" Letters to nature, pp. 488-491, vol. 369, 1994.
Hutton, M., et al., "Association of missense and 5'-splice-site mutations in tau with the inherited dementia FTDP-17" Nature, Jun. 18, 1998, pp. 702-705, vol. 393.
Ishihara, T., et al., "Age-dependent emergence and progression of a tauopathy in transgenic mice overexpressing the shortest human tau isoforms" Neuron, Nov. 1999, pp. 751-762, vol. 24.
Ito, A. et al., "Enhancing effect of ascorbate on toluidine blue-photosensitization of yeast cells" Photochemistry and Photobiology, (1982), pp. 501-505, vol. 35.
Li, J et al., "Rifampicin inhibits α-Synuclein fibrillation and disaggregates fibrils" Chemistry and Biology, Nov. 2004, pp. 1513-1521, vol. 11.
Link, E.M."Targeting melanoma with 211At/1311-methylene blue: preclinical and clinical experience" Hybridoma 1999, pp. 77-82, vol. 18(1).

(Continued)

*Primary Examiner* — Paul Zarek
(74) *Attorney, Agent, or Firm* — Foley & Lardner LLP

(57) ABSTRACT

The invention relates generally to the use of diaminophenothiazine compounds to inhibit or reverse the aggregation of synuclein, and for their use in the manufacture of medicaments for this purpose (e.g. for the treatment of Parkinson's Disease). Also provided are related methods of detecting or labelling of aggregated synuclein.

15 Claims, 11 Drawing Sheets

OTHER PUBLICATIONS

Masuda, M., et al., Small molecule inhibitors of α-synuclein filament assembly. Biochemistry, (2006), pp. 6085-6094, 45.

Mukaetova-Ladinska, E.B. et al., "α-Synuclein inclusions in Alzheimer and Lewy body disease" Journal of Neuropathology and Experimental Neurology, May 2000, pp. 408-417, vol. 59, No. 5.

Pickhardt, M., et al., Anthraquinones inhibit tau aggregation and dissolve alzheimer paired helical filaments in vitro and in cells. Journal of Biological Chemistry 280, (2005), pp. 3628-3635.

Piotrowski, G "The treatment of parkinsonian tremor" Medical Record, pp. 322-323, 144, 1936.

Shojania, A.M. et al., "The effect of toluidine blue and methylene blue in immunochemical reactions in vitro" Clinical Immunology and Immunopathology, (1987), pp. 223-228, 43.

Taniguchi, S., et al., Inhibition of heparin-induced tau filament formation by phenothiazines, polyphenols, and porphyrins. Journal of Biological Chemistry 280, (2005), pp. 7614-7623.

Varani, L. et al., "Structure of tau exon 10 splicing regulatory element RNA and destabilization by mutations of frontotemporal dementia and parkinsonism linked to chromosome 17" Proc. Natl. Acad. Sci. USA, (1999), pp. 8229-8234, vol. 96.

Wischik, C., "Molecular neuropathology of Alzheimer's disease", (1991), pp. 239-250, John Libbey & Co.

Wischik, C.M. et al "Modelling prion-like processing of tau protein in Alzheimer's disease for pharmaceutical development" pp. 185-241, 1997.

Wischik, C.M. et al., "The role of tau protein in the neurodegenerative dementias" Dementia 2nd edition, pp. 461-492—O'Brien, J (EDT)/Ames, D (EDT)/Burns, A (EDT)/Levy, R/ Publisher: Hodder Arnold Published Feb. 2001.

Zhu, M et al., "The Flavonoid Baicalein Inhibits Fibrillation of α-Synuclein and Disaggregates Existing Fibrils" The Journal of Biological Chemistry, 2004, pp. 26846-26857, vol. 279, 26.

* cited by examiner

INHIBITORS OF PROTEIN AGGREGATION

TECHNICAL FIELD

The present invention generally concerns the aggregation of α-synuclein proteins associated with neurodegenerative disease such as Parkinson's disease (PD) and diaminophenothiazine compounds capable of modulating such aggregation.

BACKGROUND TO INVENTION

Parkinson's disease is a common human neurodegenerative movement disorder and affects 1% of the elderly population (see discussion by Kapurniotu (2004) Chemistry & Biology 11, pp 1476-1478). Primary clinical symptoms of PD are bradykinesia, resting tremor, muscular rigidity, and difficulty with balance. PD is neuropathologically characterized by a marked and progressive degeneration of dopaminergic neurons and by the presence of fibrillar cytoplasmic inclusions (Lewy bodies [LBs]) and dystrophic neurites (Lewy neurites [LNs]) in the *substantia nigra* and other regions of the brain (Recchia et al. (2004) FASEB J 18: 617-626).

Although the loss of dopamine neurons is certainly related to the major clinical symptoms of PD, the causes and the pathogenesis of this multifactorial disease as well as that of related "synucleinopathies" are still largely unknown.

The major components of both LBs and LNs are fibrillar aggregates of α-synuclein. α-Synuclein is a widely expressed, neuronal presynaptic protein that appears to play a role in membrane-associated processes and synaptic plasticity and has been linked to learning and development processes. While the mechanism(s) of formation of LBs and LNs and their association with PD are yet not understood, several lines of evidence suggest that α-synuclein fibrillization is associated with PD and that α-synuclein fibrillization causes toxicity (see e.g. Masliah et al., Science, 287:1265-1269 (2000); Feany et al., Nature 404:394-8 (2000)).

In addition to α-synuclein, β-synuclein has also been implicated in neurodegenerative synucleinopathies. Human β-synuclein is a 134-residue neuronal protein that is 78% homologous to α-synuclein. The α- and β-synucleins share a conserved C-terminus with three identically placed tyrosine residues. In addition to α-synuclein-containing LBs and LNs, the development of PD and dementia with LBs is accompanied by the appearance of novel α- and β-synuclein-positive lesions in hippocampus (Galvin et al. 1999) implicating β-synuclein, in addition to α-synuclein, in the onset and progression of these diseases. It has been indicated that β-synuclein may regulate α-synuclein fibrillation, perhaps acting as a chaperone to minimize the aggregation of α-synuclein (Hashimoto et al. 2001; Uversky et al. 2002; Park and Lansbury, 2002). Thus a decrease in the levels of β-synuclein has been considered as a possible factor in the PD etiology (Uversky et al. 2002).

Thus the inhibition or reversal of synuclein aggregation is believed to be of therapeutic benefit.

Li et al. (2004) Chemistry & Biology 11: pp 1513-1521 discuss the inhibition of α-synuclein fibrillization, and the disaggregation of fibrils, by the antibiotic rifampicin.

Zhu et al. (2004) Journal of Biological Chemistry 279, 26: pp 26846-26857 discuss the inhibition of α-synuclein fibrillization, and the disaggregation of fibrils, by the flavanoid baicalein.

There are a number of other publications in the art said to be concerned with the inhibitors of such aggregation. These include "Compositions for inhibiting the aggregation pathway of alpha-synuclein" (U.S. Pat. No. 6,780,971-2004-08-24); "Polyhydroxylated aromatic compounds for the treatment of amyloidosis and alpha-synuclein fibril diseases" (US2004152760-2004-08-05); Peptide and peptide derivatives for the treatment of alpha-synuclein related diseases (WO2004009625-2004-01-29); Proanthocyanidins for the treatment of amyloid and alpha-synuclein diseases (EP1377287-2004-01-07); Methods for preventing neural tissue damage and for the treatment of alpha-synuclein diseases (CN1440420T-2003-09-03).

However, it will be understood that the provision of compounds not previously known to be capable of inhibiting synuclein aggregation would provide a contribution to the art.

DISCLOSURE OF THE INVENTION

The present inventors have demonstrated for first the time that diaminophenothiazine compounds can be used to inhibit the aggregation of synuclein proteins.

Briefly, the inventors expressed and purified two forms of α-synuclein and used them in assays for self-assembly and fibril formation. A truncated form of α-synuclein (tsyn) was found to be particularly effective in the fibril-formation assay, and such assembled tsyn was shown to enhance the fluorescence of thioflavine T. The inventors assayed the fibril-disrupting activity of diaminophenothiazines, as well as other compounds. The diaminophenothiazines were found to disrupt assembled α-synuclein at less than 1 μM.

A solid phase assay for synuclein binding was also devised, and was used to show that diaminophenothiazines such as thioninium chlorides, and flavones, inhibited the binding.

As will be appreciated by those skilled in the art, in the light of the present disclosure, these results demonstrate utility for such compounds inter alia in the treatment of the underlying cause of diseases (such as PD and others discussed herein) associated with synuclein aggregation.

Piotrowski, G. (1936) "The treatment of parkinsonian tremor. *Medical Record,* 144:322-323" reported the symptomatic relief of Parkinsonian tremor in a study of 4 individuals using Methylene blue (methyl thioninium chloride-MTC). The MTC was administered intravenously at 1 or 2 mg/kg doses. An oral administration of 8 grains (=518 mg)/day was discontinued due to side effects. The reported effects on tremor were not strong and lasted for a limited time only, while a different symptom (rigidity) was not greatly affected. A separate test with thionin gave no result. The essence of the disclosure is thus that MTC specifically, which was known to have a parasympathetic action, had a limited effect on one symptom of Parkinson's disease i.e. the "parkinsonian tremor".

By contrast the present invention concerns a treatment directed as the underlying disease process itself rather than a symptomatic manifestation of the disease.

Diaminophenothiazines have previously been shown to inhibit tau protein aggregation and to disrupt the structure of PHFs, and reverse the proteolytic stability of the PHF core (see WO 96/30766, F Hoffman-La Roche). Such compounds were disclosed for use in the treatment of various diseases, including Alzheimer's disease and Lewy Body Disease.

Additionally WO 02/055720 (The University Court of the University of Aberdeen) discusses the use of reduced forms of diaminophenothiazines specifically for the treatment of a variety of protein aggregating diseases, although the disclosure is primarily concerned with tauopathies.

WO 2005/030676 (The University Court of the University of Aberdeen) discusses radiolabelled phenothiazines, and their use in diagnosis and therapy e.g. of tauopathies.

However none of these publications specifically disclose the use of diaminophenothiazines, particularly non-reduced forms, for the inhibition or reversal of α-synuclein aggregation in particular.

Diaminophenothiazine Compounds

The invention pertains to certain diaminophenothiazine compounds and analogs thereof, having one of the following formulae, and pharmaceutically acceptable salts, hydrates, and solvates thereof (collectively referred to herein as "diaminophenothiazines" or "diaminophenothiazine compounds"):

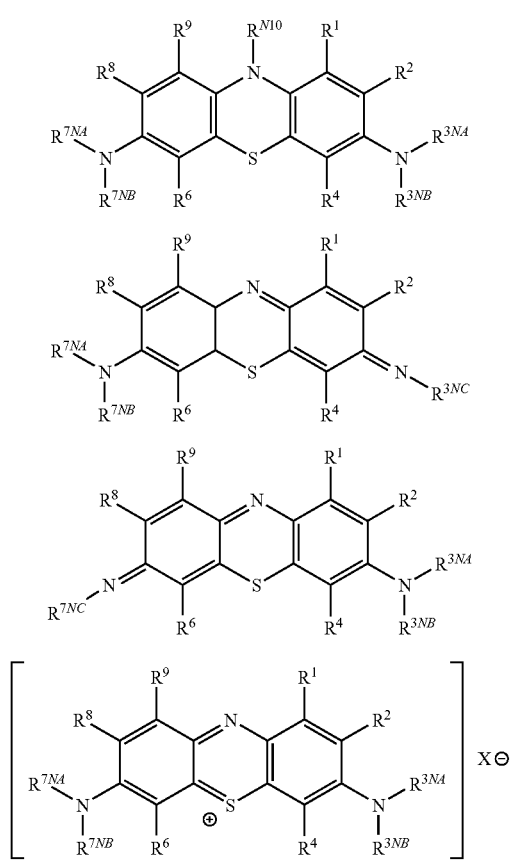

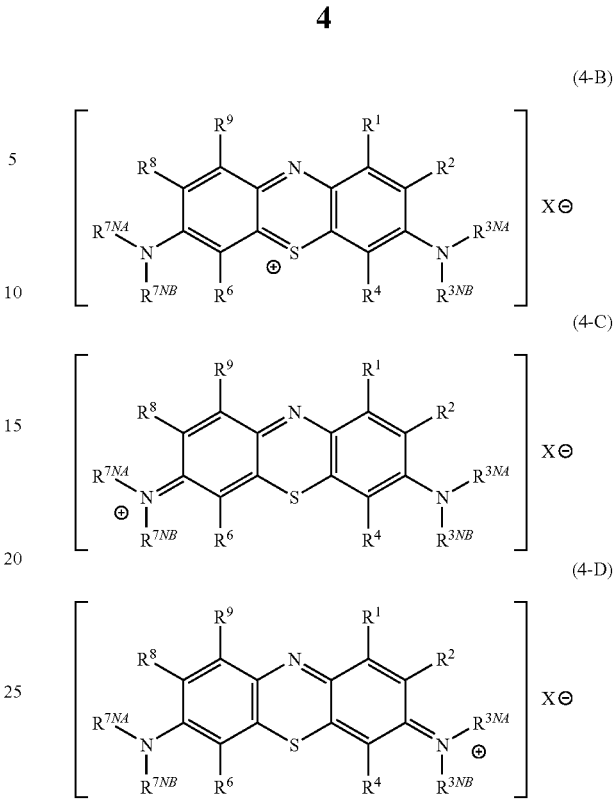

Formula (1) depicts compounds in a reduced form, whereas each of Formulae (2), (3), and (4) depicts compounds in an oxidized form.

In one embodiment, the compounds are selected from compounds of formula (1), and pharmaceutically acceptable salts, hydrates, and solvates thereof.

In one embodiment, the compounds are selected from compounds of formula (2) or (3), and pharmaceutically acceptable salts, hydrates, and solvates thereof.

In one embodiment, the compounds are selected from compounds of formula (4), and pharmaceutically acceptable salts, hydrates, and solvates thereof.

Each one of the above structures is only one of many equivalent resonance structures, and all of which are intended to be encompassed by that representative structure. For example, structure (4) is only one of many equivalent resonance structures, some of which are shown below, and all of which are intended to be encompassed by structure (4):

Carbon Ring Atom Substituents

In each one of the above formulae, each one of $R^1$, $R^2$, $R^4$, $R^6$, $R^8$, and $R^9$ is independently selected from:
—H;
—F; —Cl; —Br; —I;
—OH; —OR;
—SH; —SR;
—NO$_2$;
—C(=O)R;
—C(=O)OH; —C(=O)OR;
—C(=O)NH$_2$; —C(=O)NHR; —C(=O)NR$_2$;
—C(=O)NR$^{N1}$R$^{N2}$;
—NH$_2$; —NHR; —NR$_2$; —NR$^{N1}$R$^{N2}$;
—NHC(=O)H; —NRC(=O)H; —NHC(=O)R; —NRC(=O)R;
—R;

wherein each R is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
unsubstituted $C_{6-10}$carboaryl; substituted $C_{6-10}$carboaryl;
unsubstituted $C_{5-10}$heteroaryl; substituted $C_{5-10}$heteroaryl;
unsubstituted $C_{6-10}$carboaryl-$C_{1-4}$alkyl; substituted $C_{6-10}$carboaryl-$C_{1-4}$alkyl;

wherein, in each group —NR$^{N1}$R$^{N2}$, independently, R$^{N1}$ and R$^{N2}$ taken together with the nitrogen atom to which they are attached form a ring having from 3 to 7 ring atoms.

Examples of groups —NR$^{N1}$R$^{N2}$, wherein R$^{N1}$ and R$^{N2}$ taken together with the nitrogen atom to which they are attached form a ring having from 3 to 7 ring atoms, include: pyrrolidino, piperidino, piperazino, morpholino, pyrrolyl, and substituted forms, such as N-substituted forms, such as N-methyl piperazino.

In one embodiment, each one of $R^1$, $R^2$, $R^4$, $R^6$, $R^8$, and $R^9$ is independently selected from:
- —H;
- —F; —Cl; —Br; —I;
- —OH; —OR;
- —C(=O)OH; —C(=O)OR;
- —R.

In one embodiment, each one of $R^1$, $R^2$, $R^4$, $R^6$, $R^8$, and $R^9$ is independently selected from:
- —H;
- —R.

In one embodiment, each R is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl.

In one embodiment, each R is independently selected from:
unsubstituted aliphatic $C_{1-6}$alkyl; substituted aliphatic $C_{1-6}$alkyl.

In one embodiment, each R is independently selected from: -Me, -Et, -nPr, and -iPr.

In one embodiment, each R is independently selected from: -Me and -Et.

In one embodiment, the $C_{1-6}$alkyl group is a $C_{1-4}$alkyl group.

In one embodiment, the $C_{2-6}$alkenyl group is a $C_{2-4}$alkenyl group.

In one embodiment, the $C_{3-6}$cycloalkyl group is a $C_{3-4}$cycloalkyl group.

Examples of unsubstituted aliphatic $C_{1-6}$alkyl groups include: methyl, ethyl, n-propyl, iso-propyl, n-butyl, iso-butyl, sec-butyl, tert-butyl, n-pentyl, iso-pentyl, tert-pentyl, neo-pentyl, hexyl, iso-hexyl, etc.

Examples of unsubstituted aliphatic $C_{2-6}$alkenyl groups include: propen-1-yl, propen-2-yl, buten-1-yl, buten-2-yl, buten-3-yl, etc.

Examples of unsubstituted $C_{3-6}$cycloalkyl groups include: cyclopropyl, cyclopropyl-methyl, cyclobutyl, cyclopentyl, cyclohexyl, etc.

In one embodiment, the $C_{6-10}$carboaryl group is a $C_6$carboaryl group.

In one embodiment, the $C_{5-10}$heteroaryl group is a $C_{5-6}$heteroaryl group.

In one embodiment, the $C_{6-10}$carboaryl-$C_{1-4}$alkyl group is a $C_6$carboaryl-$C_{1-2}$alkyl group.

Examples of unsubstituted $C_{6-10}$carboaryl groups include: phenyl, naphthyl.

Examples of unsubstituted $C_{5-10}$heteroaryl groups include: pyrrolyl, thienyl, furyl, imidazolyl, oxazolyl, isoxazolyl, thiazolyl, isothiazolyl, pyrazolyl, pyridyl, pyrazinyl, pyrimidinyl, pyridazinyl.

Examples of unsubstituted $C_{6-10}$carboaryl-$C_{1-4}$alkyl groups include: benzyl, phenylethyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are independently selected from:
- —F; —Cl; —Br; —I;
- —OH; —OR';
- —SH; —SR';
- —NO$_2$;
- —C(=O)R';
- —C(=O)OH; —C(=O)OR';
- —C(=O)NH$_2$; —C(=O)NHR'; —C(=O)NR'$_2$;
- —C(=O)NR$^{t N1}$R$^{t N2}$;
- —NH$_2$; —NHR'; —NR'$_2$; NR$^{t N1}$R$^{t N2}$,
- —NHC(=O)H; —N'RC(=O)H; —NHC(=O)'R;
- —N'RC(=O)'R;
- —R';

wherein each R' is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
unsubstituted $C_{6-10}$carboaryl; substituted $C_{6-10}$carboaryl;
unsubstituted $C_{5-10}$heteroaryl; substituted $C_{5-10}$heteroaryl;
unsubstituted $C_{6-10}$carboaryl-$C_{1-4}$alkyl; substituted $C_{6-10}$carboaryl-$C_{1-4}$alkyl;

wherein, in each group —NR$^{t N1}$R$^{t N2}$, independently, R$^{t N1}$ and R$^{t N2}$ taken together with the nitrogen atom to which they are attached form a ring having from 3 to 7 ring atoms.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are independently selected from:
- —F; —Cl; —Br; —I;
- —OH; —OR;
- —C(=O)OH; —C(=O)OR;
- —R'.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from:
unsubstituted aliphatic $C_{1-6}$alkyl;
unsubstituted aliphatic $C_{2-6}$alkenyl;
unsubstituted $C_{3-6}$cycloalkyl;
unsubstituted $C_{6-10}$carboaryl;
unsubstituted $C_{5-10}$heteroaryl;
unsubstituted $C_{6-10}$carboaryl-$C_{1-4}$alkyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from:
unsubstituted aliphatic $C_{1-6}$alkyl;
unsubstituted aliphatic $C_{2-6}$alkenyl;
unsubstituted $C_{3-6}$cycloalkyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from:
unsubstituted aliphatic $C_{1-6}$alkyl; substituted aliphatic $C_{1-6}$alkyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from: -Me, -Et, -nPr, and -iPr.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from: -Me and -Et.

In one embodiment, each one of $R^1$, $R^2$, $R^4$, $R^6$, $R^8$, and $R^9$ is independently selected from: —H, -Me, -Et, -nPr, and -iPr.

In one embodiment, each one of $R^1$, $R^2$, $R^4$, $R^6$, $R^8$, and $R^9$ is independently selected from: —H, -Me, and -Et.

In one embodiment, each one of $R^1$, $R^2$, $R^4$, $R^6$, $R^8$, and $R^9$ is independently selected from: —H and -Me.

In one embodiment, all except four of $R^1$, $R^2$, $R^4$, $R^6$, $R^8$, and $R^9$ is —H.

In one embodiment, all except two of $R^1$, $R^2$, $R^4$, $R^6$, $R^8$, and $R^9$ is —H.

In one embodiment, all except one of $R^1$, $R^2$, $R^4$, $R^6$, $R^8$, and $R^9$ is —H.

In one embodiment, each of $R^1$, $R^2$, $R^4$, $R^6$, $R^8$, and $R^9$ is —H.

Amino Groups

In each one of the above formulae, in each group —NR$^{3NA}$R$^{3NB}$, if present, each one of R$^{3NA}$ and R$^{3NB}$ is independently —H or as defined above for R; or R$^{3NA}$ and R$^{3NB}$ taken together with the nitrogen atom to which they are attached form a ring having from 3 to 7 ring atoms.

For example, in one embodiment, in each group —NR$^{3NA}$R$^{3NB}$, if present, each one of R$^{3NA}$ and R$^{3NB}$ is independently as defined above for R; or R$^{3NA}$ and R$^{3NB}$ taken together with the nitrogen atom to which they are attached form a ring having from 3 to 7 ring atoms.

For example, in one embodiment, in each group —NR$^{3NA}$R$^{3NB}$, if present, each one of R$^{3NA}$ and R$^{3NB}$ is independently selected from:
- —H;
- unsubstituted aliphatic C$_{1-6}$alkyl; substituted aliphatic C$_{1-6}$alkyl;
- unsubstituted aliphatic C$_{2-6}$alkenyl; substituted aliphatic C$_{2-6}$alkenyl;
- unsubstituted C$_{3-6}$cycloalkyl; substituted C$_{3-6}$cycloalkyl;
- unsubstituted C$_{6-10}$carboaryl; substituted C$_{6-10}$carboaryl;
- unsubstituted C$_{5-10}$heteroaryl; substituted C$_{5-10}$heteroaryl;
- unsubstituted C$_{6-10}$carboaryl-C$_{1-4}$alkyl; substituted C$_{6-10}$carboaryl-C$_{1-4}$alkyl;

or R$^{3NA}$ and R$^{3NB}$ taken together with the nitrogen atom to which they are attached form a ring having from 3 to 7 ring atoms.

For example, in one embodiment, in each group —NR$^{3NA}$R$^{3NB}$, if present, each one of R$^{3NA}$ and R$^{3NB}$ is independently selected from:
- unsubstituted aliphatic C$_{1-6}$alkyl; substituted aliphatic C$_{1-6}$alkyl;
- unsubstituted aliphatic C$_{2-6}$alkenyl; substituted aliphatic C$_{2-6}$alkenyl;
- unsubstituted C$_{3-6}$cycloalkyl; substituted C$_{3-6}$cycloalkyl;
- unsubstituted C$_{6-10}$carboaryl; substituted C$_{6-10}$carboaryl;
- unsubstituted C$_{5-10}$heteroaryl; substituted C$_{5-10}$heteroaryl;
- unsubstituted C$_{6-10}$carboaryl-C$_{1-4}$alkyl; substituted C$_{6-10}$carboaryl-C$_{1-4}$alkyl;

or R$^{3NA}$ and R$^{3NB}$ taken together with the nitrogen atom to which they are attached form a ring having from 3 to 7 ring atoms.

In another example, in one embodiment, in each group —NR$^{3NA}$R$^{3NB}$, if present, each one of R$^{3NA}$ and R$^{3NB}$ is independently selected from:
- —H;
- unsubstituted aliphatic C$_{1-6}$alkyl; substituted aliphatic C$_{1-6}$alkyl;
- unsubstituted aliphatic C$_{2-6}$alkenyl; substituted aliphatic C$_{2-6}$alkenyl;
- unsubstituted C$_{3-6}$cycloalkyl; substituted C$_{3-6}$cycloalkyl;

or R$^{3NA}$ and R$^{3NB}$ taken together with the nitrogen atom to which they are attached form a ring having from 3 to 7 ring atoms.

In another example, in one embodiment, in each group —NR$^{3NA}$R$^{3NB}$, if present, each one of R$^{3NA}$ and R$^{3NB}$ is independently selected from:
- —H;
- unsubstituted aliphatic C$_{1-6}$alkyl;
- unsubstituted aliphatic C$_{2-6}$alkenyl;
- unsubstituted C$_{3-6}$cycloalkyl;

or R$^{3NA}$ and R$^{3NB}$ taken together with the nitrogen atom to which they are attached form a ring having from 3 to 7 ring atoms.

In another example, in one embodiment, in each group —NR$^{3NA}$R$^{3NB}$, if present, each one of R$^{3NA}$ and R$^{3NB}$ is independently selected from:
- unsubstituted aliphatic C$_{1-6}$alkyl;
- unsubstituted aliphatic C$_{2-6}$alkenyl;
- unsubstituted C$_{3-6}$cycloalkyl;

or R$^{3NA}$ and R$^{3NB}$ taken together with the nitrogen atom to which they are attached form a ring having from 3 to 7 ring atoms.

In another example, in one embodiment, in each group —NR$^{3NA}$R$^{3NB}$, if present, each one of R$^{3NA}$ and R$^{3NB}$ is independently selected from: —H, -Me, -Et, -nPr, and -iPr.

In another example, in one embodiment, in each group —NR$^{3NA}$R$^{3NB}$, if present, each one of R$^{3NA}$ and R$^{3NB}$ is independently selected from: —H, -Me, and -Et (e.g., —NR$^{3NA}$R$^{3NA}$ is —NH$_2$, —NHMe, —NMe$_2$, —NHEt, —NEt$_2$, or —NMeEt).

In another example, in one embodiment, in each group —NR$^{3NA}$R$^{3NB}$, if present, each one of R$^{3NA}$ and R$^{3NB}$ is independently selected from: —H and -Me (e.g., —NR$^{3NA}$R$^{3NA}$ is —NH$_2$, —NHMe, or —NMe$_2$).

In precise analogy, in each one of the above formulae, in each group —NR$^{7NA}$R$^{7NB}$, if present, each one of R$^{7NA}$ and R$^{7NB}$ is independently —H or as defined above for R; or R$^{7NA}$ and R$^{7NB}$ taken together with the nitrogen atom to which they are attached form a ring having from 3 to 7 ring atoms.

For example, in one embodiment, in each group —NR$^{7NA}$R$^{7NB}$, if present, each one of R$^{7NA}$ and R$^{7NB}$ is independently as defined above for R; or R$^{7NA}$ and R$^{7NB}$ taken together with the nitrogen atom to which they are attached form a ring having from 3 to 7 ring atoms.

In one embodiment, NR$^{3NA}$R$^{3NB}$ and —NR$^{7NA}$R$^{7NB}$, if both present, are the same.

In one embodiment, —NR$^{3NA}$R$^{3NB}$ and —NR$^{7NA}$R$^{7NB}$, if both present, are different.

In each one of the above formulae, in each group =NR$^{3NC}$, if present, R$^{3NC}$ is independently —H or as defined above for R.

For example, in one embodiment, in each group =NR$^{3NC}$, if present, R$^{3NC}$ is independently as defined above for R.

For example, in one embodiment, in each group =NR$^{3NC}$, if present, R$^{3NC}$ is independently selected from:
- —H;
- unsubstituted aliphatic C$_{1-6}$alkyl; substituted aliphatic C$_{1-6}$alkyl;
- unsubstituted aliphatic C$_{2-6}$alkenyl; substituted aliphatic C$_{2-6}$alkenyl;
- unsubstituted C$_{3-6}$cycloalkyl; substituted C$_{3-6}$cycloalkyl;
- unsubstituted C$_{2-6}$carboaryl; substituted C$_{6-10}$carboaryl;
- unsubstituted C$_{5-10}$heteroaryl; substituted C$_{5-10}$heteroaryl;
- unsubstituted C$_{6-10}$carboaryl-C$_{1-4}$alkyl; substituted C$_{6-10}$carboaryl-C$_{1-4}$alkyl.

For example, in one embodiment, in each group =NR$^{3NC}$, if present, R$^{3NC}$ is independently selected from:
- unsubstituted aliphatic C$_{1-6}$alkyl; substituted aliphatic C$_{1-6}$alkyl;
- unsubstituted aliphatic C$_{2-6}$alkenyl; substituted aliphatic C$_{2-6}$alkenyl;
- unsubstituted C$_{3-6}$cycloalkyl; substituted C$_{3-6}$cycloalkyl;
- unsubstituted C$_{6-10}$carboaryl; substituted C$_{6-10}$carboaryl;
- unsubstituted C$_{5-10}$heteroaryl; substituted C$_{5-10}$heteroaryl;
- unsubstituted C$_{6-10}$carboaryl-C$_{1-4}$alkyl; substituted C$_{6-10}$carboaryl-C$_{1-4}$alkyl.

In another example, in one embodiment, in each group =NR$^{3NC}$, if present, R$^{3NC}$ is independently selected from:

—H;
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl.

In another example, in one embodiment, in each group $=NR^{3NC}$, if present, $R^{3NC}$ is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl.

In another example, in one embodiment, in each group $=NR^{3NC}$, if present, $R^{3NC}$ is independently selected from:
—H;
unsubstituted aliphatic $C_{1-6}$alkyl;
unsubstituted aliphatic $C_{2-6}$alkenyl;
unsubstituted $C_{3-6}$cycloalkyl.

In another example, in one embodiment, in each group $=NR^{3NC}$, if present, $R^{3NC}$ is independently selected from:
unsubstituted aliphatic $C_{1-6}$alkyl;
unsubstituted aliphatic $C_{2-6}$alkenyl;
unsubstituted $C_{3-6}$cycloalkyl.

In another example, in one embodiment, in each group $=NR^{3NC}$, if present, $R^{3NC}$ is independently selected from: —H, -Me, -Et, -nPr, and -iPr.

In another example, in one embodiment, in each group $=NR^{3NC}$, if present, $R^{3NC}$ is independently selected from: —H, -Me, and -Et (e.g., $=NR^{3NC}$ is =NH, =NMe, or =NEt).

In another example, in one embodiment, in each group $=NR^{3NC}$, if present, $R^{3NC}$ is independently selected from: —H and -Me (e.g., $=NR^{3NC}$ is =NH or =NMe).

In precise analogy, in each one of the above formulae, in each group $=NR^{7NC}$, if present, $R^{7NC}$ is independently as defined above for $R^{3NC}$.

Nitrogen Ring Atom Substituent

Also, in precise analogy, in each one of the above formulae, $R^{N10}$, if present, is independently as defined above for $R^{3NC}$ (or $R^{7NC}$).

For example, in one embodiment, $R^{N10}$, if present, is independently selected from: —H and unsubstituted aliphatic $C_{1-6}$alkyl.

For example, in one embodiment, $R^{N10}$, if present, is independently selected from: —H, -Me, and -Et.

For example, in one embodiment, $R^{N10}$, if present, is independently selected from: —H and -Me.

For example, in one embodiment, $R^{N10}$, if present, is independently —H,

Counter Ion $X^-$, if present, is one or more anionic counter ions to achieve electrical neutrality.

Examples of suitable anionic counter ions are discussed below under the heading "Salts".

In one embodiment, $X^-$ is independently a halogen anion (i.e., a halide).

In one embodiment, $X^-$ is independently $Cl^-$, $Br^-$, or $I^-$.
In one embodiment, $X^-$ is independently $Cl^-$.
In one embodiment, $X^-$ is independently $NO_3^-$.

Combinations

All plausible combinations of the embodiments described above are disclosed herein as if each combination was individually and explicitly recited.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

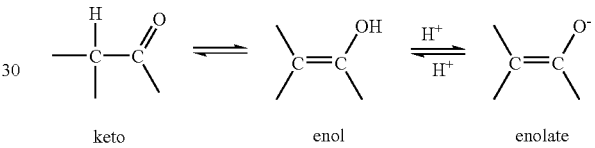

keto      enol      enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{11}C$, $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci., Vol.* 66, pp. 1-19.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$.

Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., $-NH_2$ may be $-NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

The compound may also be provided in the form of a mixed salt (i.e., the compound in combination with a salt, or another salt). For example, methyl-thioninium chloride zinc chloride mixed salt (MTZ) is a mixed salt of methyl-thioninium chloride (MTC), a chloride salt, and another salt, zinc chloride. Such mixed salts are intended to be encompassed by the term "and pharmaceutically acceptable salts thereof".

Unless otherwise specified, a reference to a particular compound also includes salt forms thereof.

Hydrates and Solvates

It may be convenient or desirable to prepare, purify, and/or handle a corresponding solvate of the active compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate forms thereof.

Some Preferred Examples

Some preferred diaminophenothiazines include the following, and pharmaceutically acceptable salts, hydrates, and solvates thereof:

A  MTC

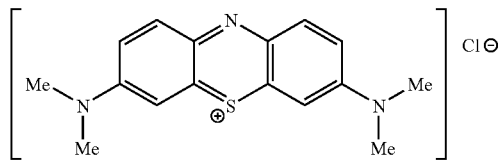

methyl-thioninium chloride

B  ETC

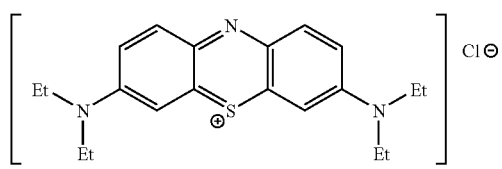

ethyl-thioninium chloride

C  DMMTC

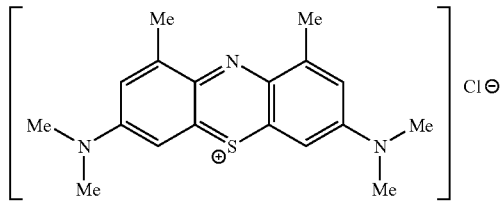

1,9-dimethyl-methyl-thioninium chloride

D  DEMTC

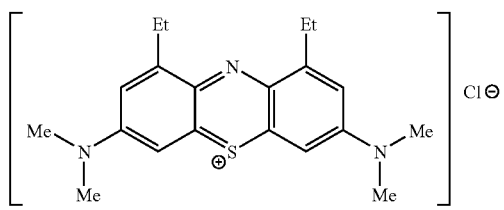

1,9-diethyl-methyl-thioninium chloride

-continued
| | | | |
|---|---|---|---|
| E | DMETC | 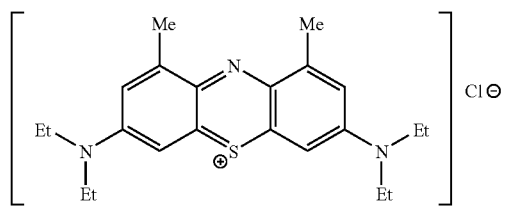 1,9-dimethyl-ethyl-thioninium chloride | |
| F | DEETC | 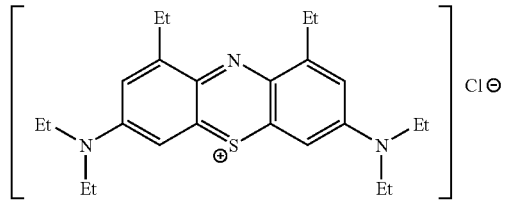 1,9-diethyl-ethyl-thioninium chloride | |
| G | MTZ | 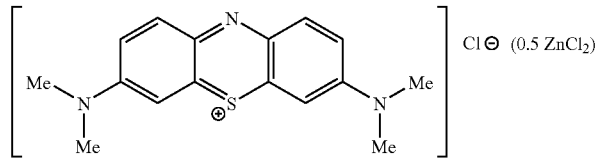 methyl-thioninium chloride zinc chloride mixed salt | |
| H | ETZ | 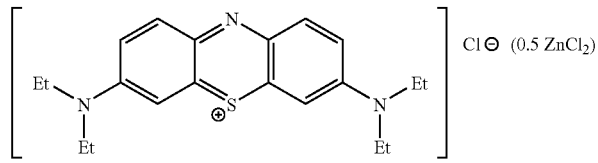 ethyl-thioninium chloride zinc chloride mixed salt | |
| I | MTI | 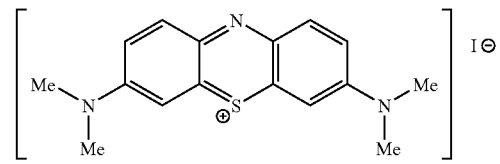 methyl-thioninium iodide | |
| J | MTI.HI | 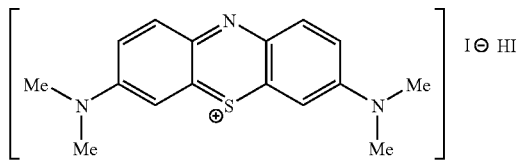 methyl-thioninium iodide hydrogen iodide mixed salt | |
| K | ETI | 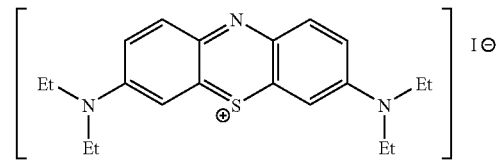 ethyl-thioninium iodide | |

-continued
| | | | |
|---|---|---|---|
| L | ETI.HI | 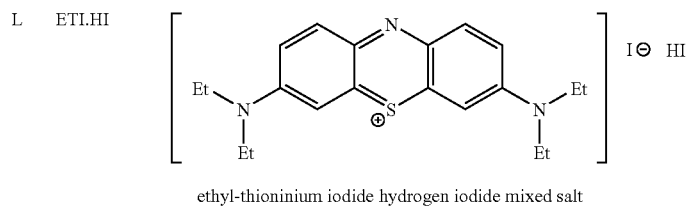 | |
ethyl-thioninium iodide hydrogen iodide mixed salt
| | | |
|---|---|---|
| M | MTN | 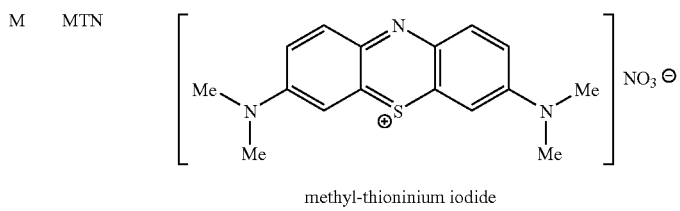 |
methyl-thioninium iodide
| | | |
|---|---|---|
| N | ETN | 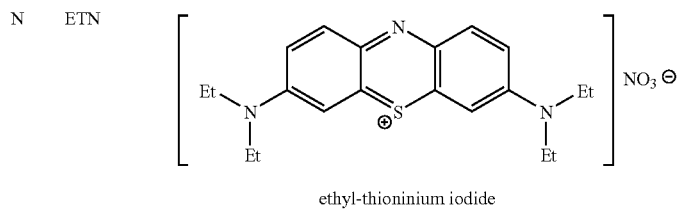 |
ethyl-thioninium iodide
| | |
|---|---|
| O | 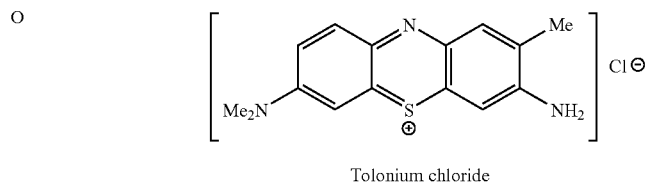 |
Tolonium chloride
| | |
|---|---|
| P | 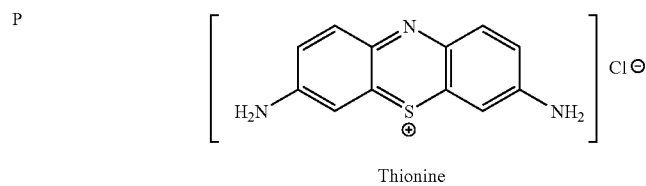 |
Thionine
| | |
|---|---|
| Q | 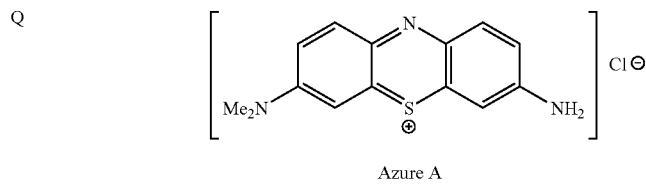 |
Azure A
| | |
|---|---|
| R | 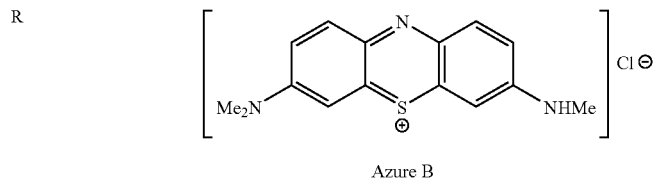 |
Azure B In one embodiment, the diaminophenothiazine is selected from: MTC, ETC, DEMTC, DEETC, Thionine, and Tolonium Chloride (also known as Toluidine Blue O).

Preferred compounds of the present invention are those which show high activity in the assays described herein.

Inhibition of Aggregation

In all therapeutic and other aspects of the invention, it is preferred that the diaminophenothiazine is in substantially oxidised form e.g. at least 50, 60, 70, 80, 90, 95, 99, or 100% oxidised form.

Thus in a first aspect of the present invention there is disclosed use of a diaminophenothiazine to inhibit the aggregation of synuclein, in particular, α-synuclein, for example in a cell.

The aggregation may be in the context of a disease state manifested as neurodegeneration and\or clinical dementia.

In another aspect, the invention provides a diaminophenothiazine for use in a method of treatment or therapy of the human or animal body, e.g., in a method of treatment or prophylaxis of a neurodegenerative disease and\or clinical dementia associated with synuclein, particularly α-synuclein, aggregation.

In another aspect, the invention provides for use of a diaminophenothiazine in the manufacture of a medicament to inhibit the aggregation of synuclein, particularly α-synuclein, which aggregation is associated with a disease state manifested as neurodegeneration and\or clinical dementia, e.g., a medicament for the treatment or prophylaxis of a neurodegenerative disease and\or clinical dementia associated with synuclein aggregation.

In another aspect, the invention provides a method of treatment or prophylaxis of a neurodegenerative disease and\or clinical dementia associated with synuclein aggregation, particularly α-synuclein, which method comprises administering to a subject a prophylactically or therapeutically effective amount of a diaminophenothiazine, or therapeutic composition comprising the same, so as to inhibit the aggregation of the synuclein.

In another aspect, the invention provides a method of regulating the aggregation of synuclein, particularly α-synuclein, in the brain of a mammal, which aggregation is associated with a disease state as described below, the treatment comprising the step of administering to said mammal in need of said treatment, a prophylactically or therapeutically effective amount of a diaminophenothiazine.

In another aspect, the invention provides a method of inhibiting production of synuclein, particularly α-synuclein, aggregates in the brain of a mammal, the treatment being as described above.

In another aspect, the invention provides a drug product for the treatment of a disease associated with synuclein, particularly α-synuclein, aggregation in a mammal suffering therefrom, comprising a container labeled or accompanied by a label indicating that the drug product is for the treatment of said disease, the container containing one or more dosage units each comprising at least one pharmaceutically acceptable excipient and, as an active ingredient, an isolated pure diaminophenothiazine compound selected from those described above.

Diaminophenothizines may be administered alone, or in combination with other treatments, either simultaneously or sequentially, dependent upon the condition or disease to be treated. In particular it may be desired to use or formulate diaminophenothiazines with other inhibitors of the relevant protein aggregation reaction.

Preferred combinations are any one or more of the diaminophenothizine compounds discussed above plus a compound that modulates dopamine levels in the mammal to be treated. Such additional compounds may include levo-DOPA and dopaminergic agonists such as ropinirole (see e.g. Olanow, C. W. 2004, The scientific basis for the current treatment of Parkinson's disease, Ann. Rev. Med. 55:41-60)

In each case, preferably the mammal is a human.

Ligands

Diaminophenothiazine compounds discussed herein that are capable of inhibiting the aggregation of α-synuclein will also be capable of acting as ligands or labels of α-synuclein (or aggregated α-synuclein). Thus, in one embodiment, the diaminophenothiazine compound is a ligand, e.g., a ligand of synuclein (or aggregated synuclein), particularly α-synuclein.

Such diaminophenothiazine compounds (ligands) may incorporate, be conjugated to, be chelated with, or otherwise be associated with, other chemical groups, such as detectable labels, such as stable and unstable detectable isotopes, radioisotopes, positron-emitting atoms, magnetic resonance labels, dyes, fluorescent markers, antigenic groups, therapeutic moieties, or any other moiety that may aid in a prognostic, diagnostic or therapeutic application.

For example, in one embodiment, the diaminophenothiazine compound is as defined above, but with the additional limitation that the compound incorporates, is conjugated to, is chelated with, or is otherwise associated with one or more (e.g., 1, 2, 3, 4, etc.) isotopes, radioisotopes, positron-emitting atoms, magnetic resonance labels, dyes, fluorescent markers, antigenic groups, or therapeutic moieties.

In one embodiment, the diaminophenothiazine compound is a ligand as well as a label, e.g., a label for α-synuclein (or aggregated α-synuclein), and incorporates, is conjugated to, is chelated with, or is otherwise associated with, one or more (e.g., 1, 2, 3, 4, etc.) detectable labels.

For example, in one embodiment, the diaminophenothiazine compound is as defined above, but with the additional limitation that the compound incorporates, is conjugated to, is chelated with, or is otherwise associated with, one or more (e.g., 1, 2, 3, 4, etc.) detectable labels.

In one embodiment, the detectable label is, or incorporates, a stable detectable isotope, an unstable detectable isotope, a radioisotope (e.g., $^{99}$Tc), a positron-emitting atom (e.g., $^{11}$C, $^{18}$F), a magnetic resonance label (e.g., $^{19}$F), a dye, a fluorescent group, or an antigenic group.

Labelled diaminophenothiazine compounds (e.g., when ligated to α-synuclein or aggregated α-synuclein) may be visualised or detected by any suitable means, and the skilled person will appreciate that any suitable detection means as is known in the art may be used.

For example, the diaminophenothiazine compound (ligand-label) may be suitably detected by incorporating a positron-emitting atom (e.g., $^{11}$C) (e.g., as a carbon atom of one or more alkyl group substituents, e.g., methyl group substituents) and detecting the compound using positron emission tomography (PET) as is known in the art.

For example, in one embodiment, the diaminophenothiazine compound is as defined above, but with the additional limitation that at least one (e.g., 1, 2, 3, 4, etc.) of the ring carbon atoms of the diaminophenothiazine compound is a positron-emitting carbon atom, e.g., $^{11}$C; and/or at least one (e.g., 1, 2, 3, 4, etc.) of the carbon atoms of at least one (e.g., 1, 2, 3, 4, etc.) of the substituents $R^1$, $R^2$, $R^4$, $R^6$, $R^8$, $R^9$, $R^{3NA}$, $R^{3NB}$, $R^{3NC}$, $R^{7NA}$, $R^{7NB}$, $R^{7NC}$, and $R^{N10}$ is a positron-emitting carbon atom, e.g., $^{11}$C.

In one embodiment, at least one (e.g., 1, 2, 3, 4, etc.) of the carbon atoms of at least one (e.g., 1, 2, 3, 4) of the substituents $R^{3NA}$, $R^{3NB}$, $R^{3NC}$, $R^{7NA}$, $R^{7NB}$, and $R^{7NC}$ is a positron emitting carbon atom, e.g., $^{11}C$.

In one embodiment, at least one (e.g., 1, 2, 3, 4, etc.) of the substituents $R^{3NA}$, $R^{3NB}$, $R^{3NC}$, $R^{7NA}$, $R^{7NB}$, and $R^{7NC}$ is —$^{11}CH_3$.

Examples of such diaminophenothiazine compounds (i.e., which incorporate a positron-emitting atom detectable by PET) include the following:

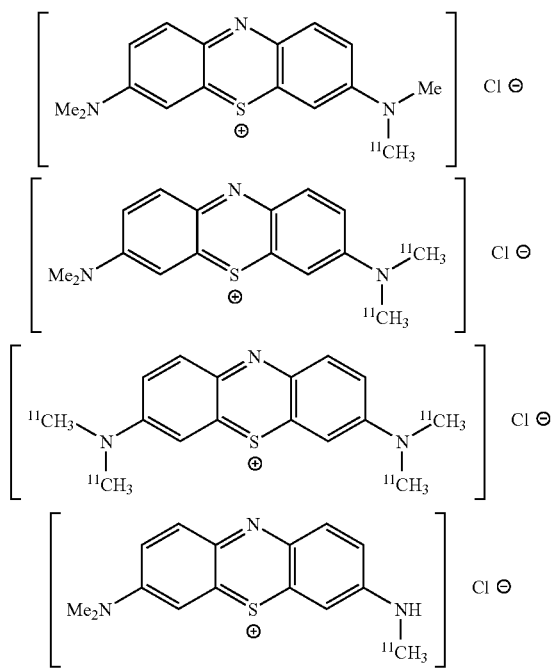

Suitable methods for preparing these and similar $^{11}C$ labelled diaminophenothiazines are shown, for example, in WO 02/075318 (see FIGS. 11a, 11b, 12) and WO 2005/030676.

Alternatively, or in addition, the diaminophenothiazine compound may be conjugated to a chelating group (i.e., a moiety suitable for conjugation to another molecule or atom or ion by complex or chelate formation) (e.g., a radioisotope-chelating group, e.g., a technetium-chelating group, e.g., a diethylenetriaminepentaacetic acid group) that is chelated to a detectable label (e.g., a radioisotope, e.g., $^{99}Tc$).

For example, in one embodiment, the diaminophenothiazine compound is as defined above, but with the additional limitation that at least one (e.g., 1, 2, 3, 4, etc.) of the substituents $R^1$, $R^2$, $R^4$, $R^6$, $R^8$, $R^9$, $R^{3NA}$, $R^{3NB}$, $R^{3NC}$, $R^{7NA}$, $R^{7NB}$, $R^{7NC}$, and $R^{N10}$ is, or incorporates, a chelating group (e.g., a technetium-chelating group, e.g., a diethylenetriaminepentaacetic acid group) that is able to chelate a detectable label (e.g., a radioisotope, e.g., $^{99}Tc$).

Alternatively, or in addition, the diaminophenothiazine compound may incorporate a magnetic resonance label (e.g., $^{19}F$), and so be suitable for MRI imaging (see e.g. Higuchi et al. Nat. Neurosci. 2005 April; 8(4):527-33).

For example, in one embodiment, the diaminophenothiazine compound is as defined above, but with the additional limitation that at least one (e.g., 1, 2, 3, 4, etc.) of the substituents $R^1$, $R^2$, $R^4$, $R^6$, $R^8$, $R^9$, $R^{3NA}$, $R^{3NB}$, $R^{3NC}$, $R^{7NA}$, $R^{7NB}$, $R^{7NC}$, and $R^{N10}$ is, or incorporates, a magnetic resonance label (e.g., $^{19}F$, for example, as —$^{19}F$, —$C(^{19}F)_3$, etc.)

Thus, in one aspect, the present invention provides a method of labelling synuclein (or aggregated synuclein), particularly α-synuclein, comprising the steps of: contacting the synuclein (or aggregated synuclein) with a diaminophenothiazine compound that incorporates, is conjugated to, is chelated with, or is otherwise associated with, a detectable label.

In another aspect, the present invention provides a method of detecting synuclein (or aggregated synuclein), particularly α-synuclein, comprising the steps of: contacting the synuclein (or aggregated synuclein) with a diaminophenothiazine compound that incorporates, is conjugated to, is chelated with, or is otherwise associated with, a detectable label, and detecting the presence and\or amount of said compound bound to synuclein (or aggregated synuclein).

In another aspect, the present invention provides a method of diagnosis or prognosis of a synucleinopathy in a subject believed to suffer from the disease, comprising the steps of:

(i) introducing into the subject a diaminophenothiazine compound capable of labelling synuclein or aggregated synuclein, particularly α-synuclein (e.g., a diaminophenothiazine compound that incorporates, is conjugated to, is chelated with, or is otherwise associated with, a detectable label), (ii) determining the presence and\or amount of said compound bound to synuclein or aggregated synuclein in the brain of the subject, (iii) correlating the result of the determination made in (ii) with the disease state of the subject.

In another aspect, the present invention provides a diaminophenothiazine compound capable of labelling synuclein or aggregated synuclein, particularly α-synuclein, (e.g., a diaminophenothiazine compound that incorporates, is conjugated to, is chelated with, or is otherwise associated with, a detectable label), for use in a method of diagnosis or prognosis of a synucleinopathy.

In another aspect, the present invention provides use of a diaminophenothiazine compound capable of labelling synuclein or aggregated synuclein, particularly α-synuclein (e.g., a diaminophenothiazine compound that incorporates, is conjugated to, is chelated with, or is otherwise associated with, a detectable label), in a method of manufacture of a diagnostic or prognostic reagent for use in the diagnosis or prognosis of a synucleinopathy.

Those skilled in the art will appreciate that instead of administering diaminophenothiazine ligands/labels directly, they could be administered in a precursor form, for conversion to the active form (e.g., ligating form, labelling form) by an activating agent present in, or administered to, the same subject.

Diseases

The disease states with which the present invention is concerned are synucleinopathies.

As those skilled in the art will be aware, the term synucleinopathies is used to name a group of neurodegenerative disorders characterized by fibrillary aggregates of synuclein protein, particularly α-synuclein, in the cytoplasm of selective populations of neurons and glia, and in particular in which the presence of synuclein-containing inclusions are pathognomic for the disease.

This should be distinguished from non-synucleinopathy disorders in which synuclein-containing inclusions may or may not be present in addition to other pathologies.

The synucleinopathies currently consist of the following disorders: Parkinson's disease (PD), dementia with Lewy bodies (DLB), multiple system atrophy (MSA), drug-induced parkinsonism (e.g. produced by 1-methyl-4-phenyl-1,2,3,6- tetrahydropyridine [MPTP] or pesticides such as rotenone), and pure autonomic failure (PAF).

Non-synucleinopathy disorders in which Lewy bodies may be found include the following: Alzheimer's disease, Pick's/frontotemporal dementia, Creutzfeldt-Jakob disease, ataxia telangectasia, corticobasal degeneration, dystonia, progressive supranuclear palsy, neuraxonal dystrophy, subacute sclerosing panencephalitis, amyotrophic lateral sclerosis, ALS-dementia Guam complex, Meige's syndrome and Hallervorden-Spatz disease (HSD) (neurodegeneration with brain iron). LBs occur commonly in a variety of neurodegenerative diseases. Studies have indicated that the morphology of α-synuclein fibrils in neuronal LBs show basic similarities regardless of the underlying disease.

Parkinson's disease has a high prevalence (ca. 100 per 100,000) compared with MSA (4 per 100,000).

DLB was adopted as the consensus name to cover several other ones that had existed earlier (McKeith, I. G. et al. (1996). "Consensus guidelines for the clinical and pathologic diagnosis of dementia with Lewy bodies (DLB): report of the consortium on DLB international workshop. Neurology, 47, 1113-1124." Neurology 47: 1113-1124). These include senile dementia of the Lewy body type, Lewy body variant of Alzheimer's disease, cortical Lewy body dementia and Lewy body dementia. MSA encompasses Shy Drager syndrome, olivopontocerebellar atrophy and striatonigral degeneration. DLB has been reported to be the second most common form of dementia in the elderly after Alzheimer's disease.

Parkinson's disease is characterised by LBs in *substantia nigra*, but they may also be found in cortex. DLB is characterised by more frequent occurrence of cortical LBs. In MSA, filamentous inclusions, termed glial cytoplasmic inclusions (GCIs) are found mainly in oligodendrocytes. The nature of the component filaments in LBs was unknown until 1997, when two findings established the major component: (i) a missense mutation in α-synuclein was found to cause a rare form of familial PD (Polymeropoulos, M. H. et al. (1997). "Mutation in the α-synuclein gene identified in families with Parkinson's disease." Science 276: 2045-2047) and (ii) LBs and LNs in idiopathic PD and in DLB were found to be immunoreactive for α-synuclein (Spillantini, M. G. et al. (1997). "α-Synuclein in Lewy bodies." Nature 388: 839-840). Recombinant α-synuclein can form filaments in vitro. The protein is a natively unfolded protein. In diseases where it aggregates, it forms fibrils with β-sheet structure.

Preferably the compounds of the present invention are used in respect of a synucleinopathy selected from PD, PAF, MSA and HSD.

Choice of Subject

The ligands disclosed herein may be used as part of a method of diagnosis or prognosis. It may be used to select a patient for treatment, or to assess the effectiveness of a treatment or a therapeutic e.g. an inhibitor of α-synuclein association administered to the subject.

Suitable subjects for the method may be selected on the basis of conventional factors. Thus the initial selection of a patient may involve any one or more of: rigorous evaluation by experienced clinician; exclusion of non-AD diagnosis as far as possible by supplementary laboratory and other investigations; objective evaluation of level of cognitive function using neuropathologically validated battery.

Dosage Units, and Formulation and Administration of Compounds

Administration of compounds, compositions or medicaments as described herein is preferably in a "prophylactically effective amount" or a "therapeutically effective amount" (as the case may be, although prophylaxis may be considered therapy), this being sufficient to show benefit to the individual.

For ligands the amount will be a diagnostically effective amount which will give rise to detectable binding in the patient suffering from a synucleinopathy.

For medicaments the actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

Typically the mammal will be human, although use in animals (e.g. for test purposes, or veterinary therapeutic purposes) is also embraced by the invention.

Example phenothiazines of the present invention are known in the art and may be manufactured by the processes referred to in standard texts (e.g. Merck Manual, Houben-Weyl, Beilstein E III/IV 27, 1214 ff, J. Heterocycl. Chem. 21, 613 (1984), etc.). The compounds of the above formulae, their pharmaceutically acceptable salts, or other compounds found to have the properties defined in the assays provided, could be used as medicaments after further testing for toxicity (e.g. in the form of pharmaceutical preparations).

The prior pharmaceutical use of methylene blue in a wide range of medical indications has been described, including treatment of methaemoglobineamia and the prophylaxis of manic depressive psychosis (Naylor (1986) Biol. Psychiatry 21, 915-920), and CNS penetration following systemic administration has been described (Muller (1992) Acta Anat., 144, 39-44). The production of Azure A and B occur as normal metabolic degradation products of methylene blue (Disanto and Wagner (1972a) J. Pharm. Sci. 61, 598-602; Disanto and Wagner (1972b) J. Pharm. Sci. 61 1086-1094). The administration of pharmaceuticals can be effected parentally such as orally, in the form of tablets, coated tablets, dragees, hard and soft gelatine capsules, solutions, emulsions or suspensions), nasally (e.g. in the form of nasal sprays) or rectally (e.g. in the form of suppositories). However, the administration can also be effected parentally such as intramuscularly or intravenously (e.g. in the form of injection solutions).

The compositions may include, in addition to the above constituents, pharmaceutically-acceptable excipients, preserving agents, solubilizers, viscosity-increasing substances, stabilising agents, wetting agents, emulsifying agents, sweetening agents, colouring agents, flavouring agents, salts for varying the osmotic pressure, buffers, or coating agents. Such materials should be non-toxic and should not interfere with the efficacy of the active ingredient. The precise nature of the carrier or other material may depend on the route of administration. Examples of techniques and protocols can be found in *"Remington's Pharmaceutical Sciences"*, $16^{th}$ edition, Osol, A. (ed.), 1980.

Where the composition is formulated into a pharmaceutical composition, the administration thereof can be effected parentally such as orally, in the form of powders, tablets, coated tablets, dragees, hard and soft gelatine capsules, solutions, emulsions or suspensions), nasally (e.g. in the form of nasal sprays) or rectally (e.g. in the form of suppositories). However, the administration can also be effected parentally such as intramuscularly, intravenously, cutaneously, subcutaneously, or intraperitoneally (e.g. in the form of injection solutions).

Thus, for example, where the pharmaceutical composition is in the form of a tablet, it may include a solid carrier such as gelatine or an adjuvant. For the manufacture of tablets, coated tablets, dragees and hard gelatine capsules, the active compounds and their pharmaceutically-acceptable acid addition salts can be processed with pharmaceutically inert, inorganic or organic excipients. Lactose, maize, starch or derivatives thereof, talc, stearic acid or its salts etc. can be used, for example, as such excipients for tablets, dragees and hard gelatine capsules. Suitable excipients for soft gelatine capsules are, for example, vegetable oils, waxes, fats, semi-solid and liquid polyols etc. Where the composition is in the form of a liquid pharmaceutical formulation, it will generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may also be included. Other suitable excipients for the manufacture of solutions and syrups are, for example, water, polyols, saccharose, invert sugar, glucose, trihalose, etc. Suitable excipients for injection solutions are, for example, water, alcohols, polyols, glycerol, vegetable oils, etc. For intravenous, cutaneous or subcutaneous injection, or intracatheter infusion into the brain, the active ingredient will be in the form of a parenterally-acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers and/or other additives may be included, as required.

Uses of the compounds herein as ligands may utilise similar carriers or compositions.

Thus in aspects of the invention wherein a diaminophenothiazine (for example MTC) is used in a method of treatment or therapy of the human or animal body, that method will preferably involve administration of the effective amount of diaminophenothiazine orally.

Preferably the medicament is adapted for oral administration, and preferably is in solid dosage unit form.

Preferably the dosage will be administered orally. Preferably it will be less than or equal to 400, 300, 200, or 100 mg daily total dose. For example it may consist of dosage units of 10, 20, 30, 40, 50, 60, 60, 80, 90, 100, 110, 120, or 130 mg t.i.d. (three times a day)

Alternatively it may consist of dosage units of 10, 20, 30, 40, 50, 60, 60, 80, 90, 100, 110, 120, 130, 140, 150, 160, 170, 180, 190, or 200 mg b.i.d. (twice a day).

Preferably the treatment is continued for equal to or at least 2, 3, or 4 weeks.

Instructions in respect of these dosages may be included in written form on or within the container of a drug product of the invention.

Where administration is in intravenous, it is preferred that the diaminophenothiazine is not MTC.

The disclosure of any cross-reference made herein, inasmuch as it may be required by one skilled in the art to supplement the present disclosure, is hereby specifically incorporated herein.

The invention will now be further described with reference to the following non-limiting Figures and Examples. Other embodiments of the invention will occur to those skilled in the art in the light of these.

FIGURES

FIG. 1: Samples from the purification of tsyn by ammonium sulphate fractionation and Ni-affinity chromatography. Samples were analysed by 15% SDS-PAGE and staining with Coomassie Blue.

FIG. 2. Samples from the purification of fsyn by ammonium sulphate fractionation and DEAE-Sepharose anion exchange chromatography. Samples were analysed by 15% SDS-PAGE and staining with Coomassie Blue.

FIG. 3. Samples from the purification of fsyn by DEAE-Sepharose anion exchange and CM-Sepharose cation exchange chromatography. Samples were analysed by 15% SDS-PAGE and staining with Coomassie Blue.

FIG. 4. Time course of fibril formation by tsyn and fsyn monitored by fluorescence of thioflavine T and primulin. tsyn-8 at 1 mg/ml (A) and fsyn-14 (B) at 2 mg/ml in 20 mM Tris.HCl, pH 7.5, plus 50 µg/ml heparin where indicated, were incubated at 37° C. with mixing. Fibril formation was assayed by adding 10 µl of the incubation to 100 µl total of 1 µM thioflavine T or primulin and the excitation spectra were measured, with the emission wavelength at 480 nm. The signal for the fluorophore alone was subtracted from the spectra before measurement of the signal at the excitation peak (420 nm for primulin, 450 nm for thioflavine T).

FIG. 5. The effect of MTC and ETC on the fluorescence of thioflavine T or primulin induced by assembled tsyn. Tsyn-13 at 1 mg/ml (~95 µM) plus 50 µg/ml heparin was incubated at 37° C. for 20 h, then aliquots were mixed with MTC (A, C) or ETC (B, D) to give the concentrations shown (µM) and incubated a further 1 h. 10 µl of the protein was added to 100 µl total volume of 1 µM thioflavine T (A, B) or primulin (C, D) and the excitation spectra were measured, with the emission wavelength at 480 nm. The traces shown are the result of subtracting the signal for the fluorophore plus compound from the signal for protein plus fluorophore and compound.

FIG. 6. The effect of MTC and ETC on the fluorescence of primulin induced by assembled fsyn-14. Protein at 2 mg/ml (~140 µM) plus 50 µg/ml heparin was incubated at 37° C. for 47 h, then aliquots were mixed with MTC (A, C) or ETC (B, D) to give the concentrations shown (µM) and incubated a further 1 h. 10 µl of the protein was added to 100 µl total volume of primulin and the excitation spectra were measured, with the emission wavelength at 480 nm. The traces shown are the result of subtracting the signal for the fluorophore plus compound from the signal for protein plus fluorophore and compound.

FIG. 7. The effect of MTC and ETC on the fluorescence of thioflavine T or primulin induced by assembled tsyn or fsyn. Fluorescence values were measured from the traces shown in FIG. 5 for tsyn-8 (A) or FIG. 6 for fsyn-14 (B) and normalised to the value measured without compound.

FIG. 8. The effect of MTC and ETC on the fluorescence of thioflavine T or primulin induced by assembled tsyn, assayed at different concentrations of thioflavine T and primulin. Tysn-16 was assembled and assayed for the effect of MTC or ETC as described for FIG. 5, except that thioflavine T and primulin were at 0.2, 1 or 5 µM. Peak fluorescence values after correction for background were normalized to the value measured without compound and are plotted as a function of concentration of compound. The effect of MTC (A, B) or ETC (C, D) was monitored with thioflavine T (A, C) or primulin (B, D).

FIG. 9. Binding of aqueous phase fsyn to solid phase tsyn. fsyn-20 at 0-10 µM was incubated with tsyn-13 bound on the solid phase at 0-2 µM and bound fsyn was detected using antibody 211.

FIG. 10. The effect of compounds on synuclein-synuclein binding. Aqueous phase fsyn-10 at 5 µM was incubated with tsyn-13 at 1 µM in the solid phase in the presence of the compounds shown.

FIG. 11. The inhibitory effect of MTC. tsyn (1 mg/ml in 20 mM Tris.HCl, pH 7.5+50 µg/ml heparin) was assembled at 37° C. for 24 hr. MTC inhibits tsyn assembly at concentrations greater than 5) μM (°, open circles). fsyn was assembled under the same conditions, except that the concentration of fsyn was 2 mg/ml and incubation was for 120 hr. MTC shows a greater inhibitory effect with fsyn than with tsyn, with inhibition occurring at 0.05) μM with the former (●, closed circles).

FIG. 12. This figure shows that at later stages of assembly (160 h) when the thioflavine T signal has reached a plateau, the thioflavine T signal is more sensitive to inhibition by MTC than the primulin signal, with a significant effect being observed at 0.05 μM.

FIG. 13. Inhibitory action of DEETC on SSFsyn expression in NIE cells. Each drug concentration (0-100 nM) was carried out in triplicate. DEETC added with dbcAMP and cells analysed after 2 days by immunoblot with mAb 42.

FIG. 14. Presence of additional protein bands that are detected with mAb 42 but not by mAb 211. Lane 1, untreated; lanes 2, 3, 4, three independent plates which were differentiated using dbcAMP.

FIG. 15. Aggregated α-synuclein in NIE cells expressing SSFsyn. Left panel, SSFsyn cells; right panel, non-transfected, control NIE-115 cells after dbcAMP treatment.

FIG. 16. Aggregated α-synuclein in NIE cells expressing SSFsyn. SSFsyn cells stained with Texas red-labelled anti-α-synuclein (left); right panel, primulin labelling; middle panel, merged image showing co-localisation of antibody and primulin labelling.

FIG. 17. The effect of MTC on the polymerisation of tsyn. tsyn-16 at 1 mg/ml (95 μM) in 20 mM Tris.HCl pH 7.5, 50 μg/ml heparin was incubated at 37° C. with mixing, in the presence of MTC at the concentrations shown. Samples (10 μl) were taken at various times and assayed for their effect on the fluorescence of either thioflavine T (upper panel) or primulin (lower panel) at 1 μM.

FIG. 18. Binding curves for different syn preparations. Tsyn-13 at 1 μM bound to ELISA plates was incubated with dilution series of three different syn preparations as shown. The aqueous phase buffer was 20 mM Tris.HCl, 50 mM NaCl, pH 7.5, 0.05% Tween-20, 1% fish skin gelatine.

FIGS. 19A and 19B: Binding curves for syn-10 in different buffers. Tsyn-13 at 1 μM bound to ELISA plates was incubated with dilution series of syn-10. The aqueous phase buffers were all 20 mM, and included 50 mM NaCl, 0.05% Tween-20, 1% fish skin gelatine.

FIG. 20: Binding curves for different syn preparations. Tsyn-13 at 1 μM bound to ELISA plates was incubated with dilution series of syn preparations as shown. The aqueous phase buffer was 20 mM Tris.HCl, pH 7.0, 50 mM NaCl, 0.05% Tween-20, 1% fish skin gelatine.

FIG. 21: Binding curves for different syn preparations. Tsyn-13 at 1 μM bound to ELISA plates was incubated with dilution series of syn preparations as shown. The aqueous phase buffer was 20 mM Tris.HCl, pH 7.0, 50 mM NaCl, 0.05% Tween-20, 1% fish skin gelatine.

FIG. 22. Binding curves for fsyn-20 and fsyn-22 in different buffers. A. Tsyn-13 at 1 μM bound to ELISA plates was incubated with dilution series of fsyn-20 in 20 mM Tris pH 7.0 or 50 mM Na phosphate pH 6.0 or 5.5. B. Tsyn-13 at 1 μM bound to ELISA plates was incubated with dilution series of fsyn-20 or fsyn-22 in Na phosphate pH 6.0. In both cases, buffers also contained 50 mM NaCl, 0.05% Tween-20 and 1% fish skin gelatine.

EXAMPLES

Chemical Synthesis

The following syntheses are provided solely for illustrative purposes and are not intended to limit the scope of the invention, as described herein.

Synthesis 1

Ethyl-thioninium chloride (ETC)

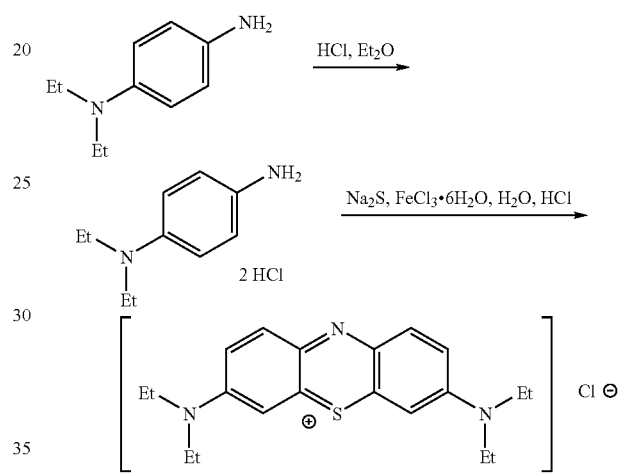

N,N-diethyl-p-phenylenediamine dihydrochloride

N,N-diethyl-p-phenylenediamine (5 g, 30.4 mmol) was dissolved in diethyl ether (25 cm$^3$) and hydrochloric acid (6 cm$^3$, 10 M) was added and the mixture was concentrated to give the title compound (7.22 g, 100%) as a red/brown solid. $\delta_H$ (250 MHz; D$_2$O): 7.68 (4H, m, ArH), 3.69 (4H, q, 7.32, NCH$_2$), 1.11 (6H, t, 7.32, CH$_3$); $\delta_C$ (62.9 MHz; D$_2$O): 12.1 (CH$_3$), 56.4 (NCH$_2$), 126.8 (ArC), 127.6 (ArC), 135.5 (ArC), 139.1 (ArC).

Ethyl-Thioninium Chloride

N,N-diethyl-p-phenylenediamine dihydrochloride (7.22 g, 30.4 mmol) was dissolved in water (250 cm$^3$) and the pH adjusted to 1.6 with HCl, to which sodium sulphide (>60%) (3.95 g, 30.4 mmol) was added portionwise. The suspension was stirred until all the sodium sulphide had dissolved. A solution of iron (III) chloride (27.15 g, 100 mmol) in water (200 cm$^3$) was prepared and half the solution was added to the mixture. An immediate colour change from light yellow to blue occurred. The solution was then aerated for 1 hour before the remaining iron (III) chloride solution was added. The mixture was cooled to 5° C. and filtered to remove a light green sludge. Aqueous HCl (15 cm$^3$, 6 M) was added to the filtrate, followed by sodium chloride (60 g), and the suspension stirred for 5 minutes before filtering to give a solid product, which was dissolved in DCM, dried over magnesium sulphate, filtered, and concentrated to give a purple/green solid (1.28 g, 22%). This purple/green solid was loaded onto a prepared C18 reverse phase column and washed with water (1 L) or until the yellow colour ceased. The product was washed off the column with MeOH/HCl (pH 2) and concentrated to give the title compound (0.64 g, 11%) as a sticky purple solid. $\delta_H$ (250 MHz; D$_2$O): 1.26 (12H, t, 6.5, CH$_3$), 3.56 (8H, q, 6.5, NCH$_2$), 7.01 (2H, s, ArH), 7.20 (2H, d, 9.25, ArH), 7.54 (2H, d, 9.25, ArH); m/z (ESI) 340.2 (100%, [M-Cl]$^+$).

Synthesis 2

1,9-Dimethyl-methyl-thioninium chloride (DMMTC)

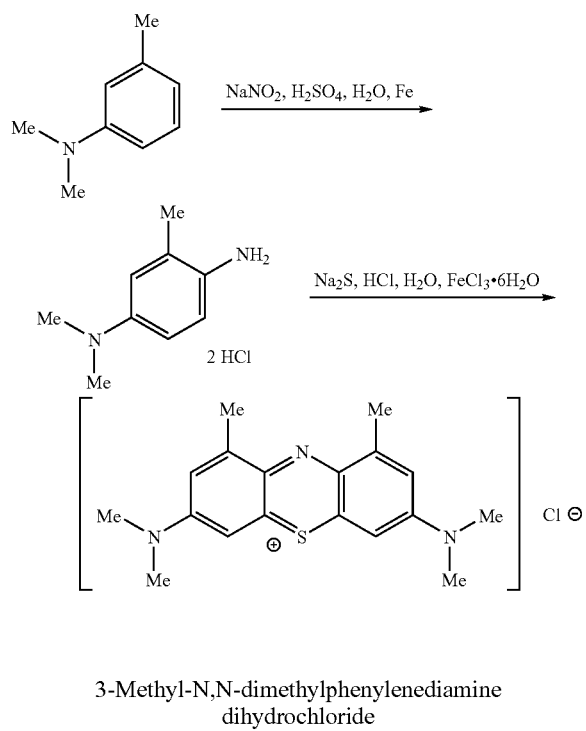

3-Methyl-N,N-dimethylphenylenediamine dihydrochloride

To a 250 cm$^3$ round bottom flask was added water (100 cm$^3$) and the temperature was reduced to 5° C. with an ice bath. To this cooled solution was carefully added sulphuric acid (98%, 22.5 g). To this solution was added 3-methyl-N,N-dimethylaniline (10 g, 74 mmol) and then sodium nitrite (5.6 g, 81.4 mmol), and the solution was stirred at room temperature for 1 hour. Iron (Fe) filings (12.8 g, 229 mmol) were added and the mixture stirred for a further 2 hours. The solution was filtered and then neutralized with saturated sodium hydrogen carbonate solution and the organics were extracted into ethyl acetate (3×100 cm$^3$). The extracts were dried over magnesium sulphate, filtered, and concentrated to give a brown oil. The oil was dissolved in diethyl ether (100 cm$^3$) and concentrated hydrochloric acid (50 cm$^3$) was added. The solution was evaporated to dryness to give the title compound (10 g, 60%) as a light tan solid. $\nu_{max}$(KBr)/cm$^{-1}$: 2849 (CH), 2821 (CH), 2543 (CM, 2444 (CA), 1586 (C=N), 1487 (CH), 1445 (CH), 1415 (CH), 1138 (CH); $\delta_H$ (250 MHz; D$_2$O): 7.59 (1H, s, ArH), 7.50 (2H, s, ArH), 3.24 (6H, s, CH$_3$), 2.39 (3H, s, CH$_3$); $\delta_C$ (62.9 MHz; D$_2$O) 18.9 (CH$_3$), 48.8 (CH$_3$), 122.1 (ArC), 126.2 (ArC), 127.6 (ArC), 133.7 (ArC), 137.4 (ArC), 144.4 (ArC).

Dimethylmethylhioninium Chloride

To a 500 cm$^3$ round bottom flask was added 3-methyl-N,N-dimethyl-phenylene-diamine dihydrochloride (0.9 g, 4.03 mmol) which was dissolved in aqueous hydrochloric acid (50 cm$^3$, 3 M) before sodium sulphide (>60%) (0.52 g, 4.03 mmol) was added. Iron (III) chloride hexahydrate (7.26 g, 27 mmol) was dissolved in water (50 cm$^3$) and half of this solution was poured into the reaction mixture, giving an immediate blue colour. The solution was then aerated for 2 hours before the remaining aqueous iron (III) chloride solution was added. The mixture was cooled to 5° C. and filtered; the precipitate was dissolved in boiling water (60 cm$^3$), filtered, and cooled. Hydrochloric acid (10 cm$^3$, 6 M) was added to the cooled solution, which was then filtered to yield the title compound (0.22 g, 16%) as a purple/blue solid. $\nu_{max}$ (KBr)/cm$^{-1}$: 2926 (CH), 1604 (C=N), 1535, 1496, 1444 (CH), 1404 (CH), 1315 (CH), 1185 (CH); $\delta_H$ (250 MHz; DMSO): 7.29 (2H, s, ArH), 7.23 (2H, s, ArH), 3.29 (12H, s, CH$_3$), 2.55 (6H, s, CH$_3$); $\delta_C$ (62.9 MHz; DMSO): 18.9 (CH$_3$), 41.5 (CH$_3$), 105.7 (ArC), 118.7 (ArC), 133.6 (ArC), 134.5 (ArC), 147.2 (ArC), 154.2 (ArC); Anal. Calcd. for C$_{18}$H$_{22}$N$_3$S.3H$_2$O: C, 51.98; H, 6.74; N, 10.11; S, 7.70. Found: C, 52.03; H, 6.59; N, 10.05; S, 7.66.

Synthesis 3

1,9-Diethyl-methyl-thioninium chloride (DEMTC)

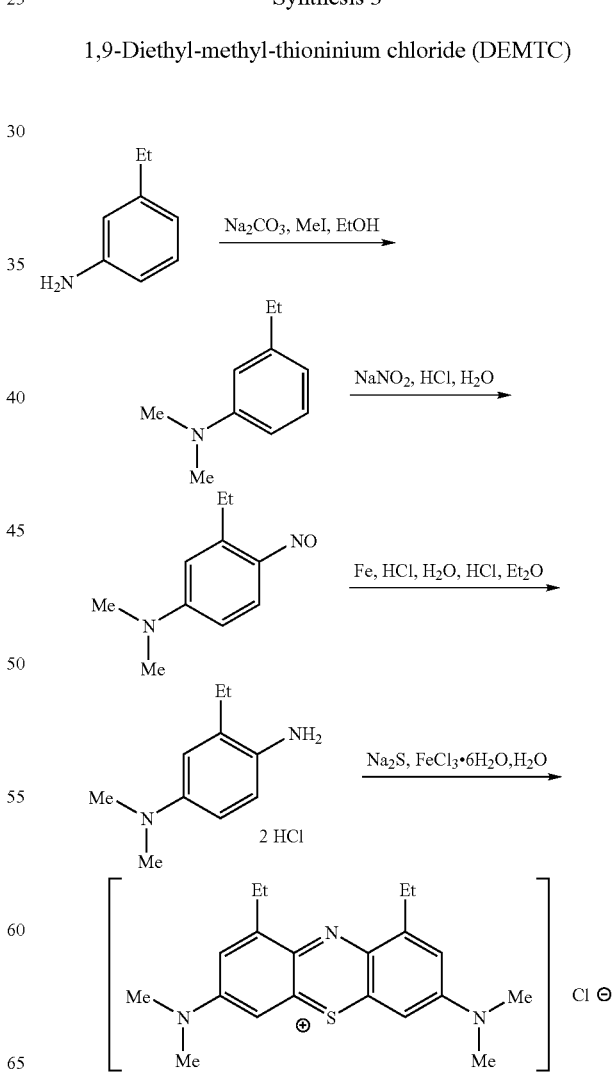

N,N-Dimethyl-m-ethylaniline

To a 100 cm³ round bottom flask was added 3-ethylaniline (10 g, 82.5 mmol), ethanol (15 cm³), sodium carbonate (11.81 g, 111.4 mmol). Methyl iodide (31.63 g, 222 mmol) was added dropwise. The mixture was then heated at 45° C. for 10 hours before cooling to room temperature and adding water (100 cm³). The mixture was extracted into diethyl ether (3×100 cm³) and the extracts were dried over magnesium sulphate, filtered, and concentrated to give the title compound (4.68 g, 38%) as a light yellow oil. $v_{max}$ (neat)/cm⁻¹: 3045 (CH), 2960 (CH), 2920 (CH), 2891 (CH), 2797 (CH), 1597 (C=N), 1494 (CH), 1438 (CH), 1352 (CH), 1225 (CH); $\delta_H$ (250 MHz; CDCl₃): 7.22 (1H, t, 7.75, ArH), 6.63 (3H, m, ArH), 2.97 (6H, s, NCH₃), 2.63 (2H, q, 7.5, CH₂), 1.27 (3H, t, 7.5, CH₃); $\delta_C$ (62.9 MHz; CDCl₃): 15.8 (CH₃), 29.5 (NCH₂), 40.8 (NCH₃), 110.3 (ArC), 112.4 (ArC), 116.5 (ArC), 129.1 (ArC), 145.3 (ArC), 150.9 (ArC).

N,N-Dimethyl-m-ethyl-p-phenylenediamine dihydrochloride

To a 250 cm³ round bottom flask was added N,N-dimethyl-m-ethylaniline (4.68 g, 31.3 mmol), water (100 cm³) and hydrochloric acid (8.5 cm³, 37%) and the solution was cooled to 5° C. An aqueous (80 cm³) solution of sodium nitrite (2.46 g, 3.57 mmol) was then added dropwise to the aniline mixture and stirred for 3 hours at room temperature. Iron (Fe) fillings (5.24 g, 94 mmol) and hydrochloric acid (8.5 cm³, 37%) were added and the mixture was stirred at room temperature for 3 hours. The suspension was filtered and the filtrate adjusted to pH 7 with sodium bicarbonate solution before extraction into ethyl acetate (3×50 cm³). The combined extracts were dried over magnesium sulphate, filtered, and concentrated to yield a brown oil. The oil was dissolved in ethanol (100 cm³) and diethyl ether (80 cm³) and hydrochloric acid (7 cm³, 37%) was added carefully to give the title compound (7.42 g, 72%) as a light tan solid. $v_{max}$ (KBr)/cm⁻¹: 2976 (CH), 2894 (CH), 2859 (CH), 2753 (CH), 1583 (C=N), 1508 (CH), 1486 (CH), 1459 (CH), 1183 (CM); $\delta_H$ (250 MHz; D₂O): 7.66 (1H, s, ArH), 7.56 (2H, s, ArH), 3.29 (6H, s, NCH₃), 2.74 (2H, q, 7.5, CH₂), 1.25 (3H, t, 7.5, CH₃); $\delta_C$ (62.9 MHz; CDCl₃): 15.5 (CH₃) 25.6 (NCH₂), 48.9 (NCH₃), 122.1 (ArC), 124.6 (ArC), 128.1 (ArC), 132.6 (ArC), 143.3 (ArC), 144.9 (ArC).

1,9-Diethyl Methylthioninium chloride

N,N-Dimethyl-m-ethyl-p-phenylenediamine dihydrochloride (1.3 g, 5.5 mmol) was dissolved in water (50 cm³) and the solution adjusted to pH 1.6. Sodium sulphide >60% (0.71 g, 5.5 mmol) was then added portionwise to the pink solution. To the suspension was added an aqueous solution of iron (III) chloride (2.23 g, 8.2 mmol in 50 cm³ of water) and there was an immediate colour change to purple. The solution was then aerated for 1 hour before a second portion of iron (III) chloride solution (2.23 g, 8.2 mmol in 50 cm³ of water) was added. The solution was cooled to 5° C. before filtering and washing the precipitate with water. To the filtrate was added sodium chloride (50 g) and the solution was stirred for 10 minutes, and the colour changed to red/purple as the product was salted out. The suspension was filtered and the solid dissolved in dichloromethane (100 cm³) and methanol (10 cm³) before drying over magnesium sulphate. Filtration and concentration gave the title compound (0.15 g, 15%) as a green solid. $v_{max}$ (KBr)/cm⁻¹: 3408 (CH), 2613 (CH), 1606 (C=N), 1399 (CH), 1316 (CH); $\delta_H$ (250 MHz; D₂O): 6.55 (2H, s, ArH), 6.23 (2H, s, ArH), 2.92 (12H, s, NCH₃), 2.56 (4H, q, 7.5, CH₂), 0.99 (6H, t, 7.5, CH₃); (ESI), 340.4 (100%, [M—Cl]⁺). Optionally, flash column chromatography was performed to remove iron chloride residues, with 10% methanol: 90% dichloromethane as eluent and using silica 40-63µ 60 Å.

Synthesis 4

1,9-Dimethyl-ethyl-thioninium chloride (DMETC)

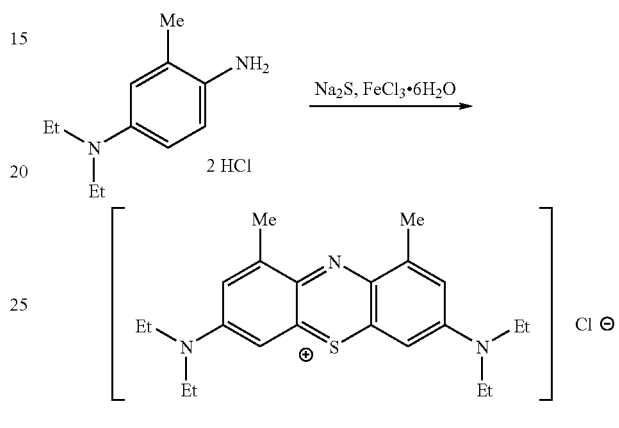

N,N-Diethyl-3-methyl-4-phenylenediamine dihydrochloride (10.74 g, 50 mmol) was dissolved in water (400 cm³) and the pH adjusted to 1.6, which then had sodium sulphide (>60%) (3.90 g, 50 mmol) added. Iron (III) chloride (20.28 g, 75 mmol) was added as an aqueous solution (175 cm³) giving an immediate colour change from yellow to deep blue. The mixture was aerated for 1 hour before a second aliquot of aqueous iron (III) chloride (20.28 g, 75 mmol in 175 cm³) was added. The solution was cooled to 5° C. and held at that temperature for 1 hour before filtering. The filtrate had sodium chloride (200 g) added and was filtered to yield the crude product as a blue/purple solid. The crude solid was purified by column chromatography (eluent being 10% MeOH, 90% DCM using silica 40-63µ 60 Å) to give the title compound (0.80 g, 4%) as a green/purple solid. $v_{max}$ (KBr)/cm⁻¹: 2971 (CH), 2921 (CH), 2865 (CH), 1600 (C=N), 1412 (CH), 1326 (CH); $\delta_H$ (250 MHz; D₂O): 6.62 (2H, s, ArH), 6.39 (2H, s, ArH), 3.30 (8H, q, NCH₂), 1.89 (6H, s, ArCH₃), 1.09 (12H, t, CH₃); $\delta_C$ (62.9 MHz; D₂O) 12.6 (CH₃), 18.0 (CH₃), 46.2 (NCH₂), 103.6 (ArC), 117.1 (ArC), 132.3 (ArC), 133.9 (ArC), 147.3 (ArC), 151.9 (ArC); m/z (ESI) 368.1 (100%, [M-Cl]⁺).

Synthesis 5

1,9-Diethyl-ethyl-thioninium chloride (DEETC)

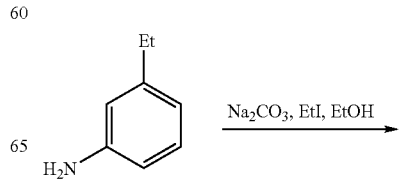

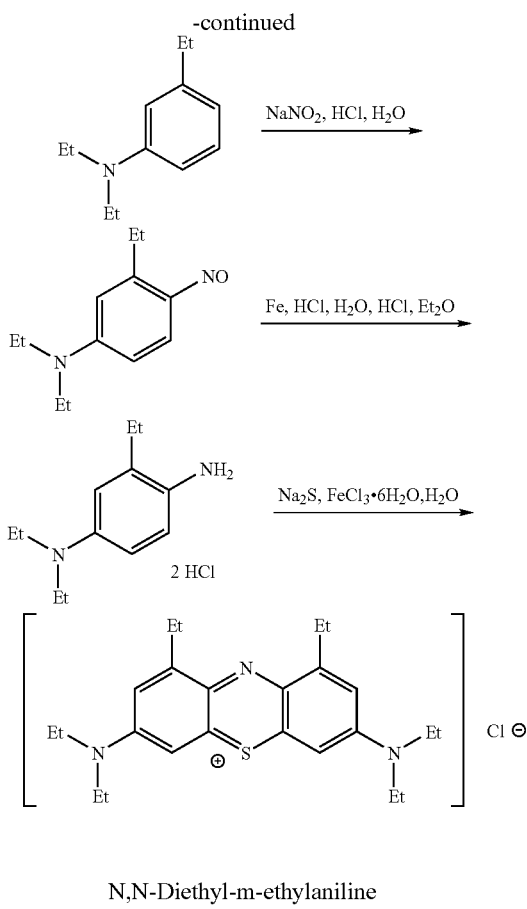

N,N-Diethyl-m-ethylaniline

To a 100 cm³ round bottom flask was added 3-ethylaniline (5.0 g, 41.3 mmol), ethanol (7.5 cm³), sodium carbonate (5.9 g, 55.7 mmol). Ethyl iodide (17.38 g, 111.4 mmol) was added dropwise. The mixture was then heated at 45° C. for 12 hours before cooling to room temperature and adding water (50 cm³). The mixture was extracted into diethyl ether (3×50 cm³) the extracts were dried over magnesium sulphate, filtered, and concentrated to give the title compound (7.03 g, 96%) as a light yellow oil. $\delta_H$ (250 MHz; CDCl₃): 7.20 (1H, dd, 9, 7.25, ArH), 6.60 (3H, m, ArH), 3.43 (4H, q, 7, NCH₂), 2.69 (2H, q, 7.25, CH₂), 1.32 (3H, t, 7.5, CH₃), 1.23 (3H, t, 7, CH₃); $\delta_C$ (62.9 MHz; CDCl₃): 12.7 (CH₃), 15.8 (CH₃), 29.5 (CH₂), 44.4 (NCH₃), 109.4 (ArC), 111.4 (ArC), 115.1 (ArC), 129.2 (ArC), 145.4 (ArC), 147.9 (ArC).

N,N-Diethyl-m-ethyl-p-phenylenediamine dihydrochloride

To a 250 cm³ round bottom flask was added N,N-diethyl-m-ethylaniline (5 g, 28.2 mmol), water (50 cm³) and hydrochloric acid (9 cm³, 37%) and the solution was cooled to 5° C. An aqueous (20 cm³) solution of sodium nitrite (2.14 g, 31.0 mmol) was then added dropwise to the aniline mixture and stirred for 1 hour at low temperature. Iron (Fe) fillings (4.72 g, 84.6 mmol) and hydrochloric acid (9 cm³, 37%) were added and the mixture stirred below 30° C. for 2 hours. The suspension was filtered and the filtrate adjusted to pH 7 with sodium bicarbonate solution before extraction into ethyl acetate (3×50 cm³). The combined extracts were dried over magnesium sulphate, filtered, and concentrated to yield a brown oil. The crude oil was purified by column chromatography (eluent being ethyl acetate using silica 40-63µ 60 Å) giving the phenylenediamine as a brown oil (2.2 g, 41%). The oil was dissolved in diethyl ether (50 cm³) and hydrochloric acid added (2.5 cm³, 37%) and the solution was concentrated to give the title compound (2.76 g, 41%) as a light brown solid. $\delta_H$ (250 MHz; D₂O): 7.50 (3H, m, ArH), 3.59 (4H, q, 7.25, NCH₂), 2.69 (2H, q, 7.5, CH₂), 1.20 (3H, t, 7.5, CH₃), 1.03 (6H, t, 7.25, CH₃); $\delta_C$ (62.9 MHz; D₂O): 12.1 (CH₃), 15.5 (CH₃), 25.5 (CH₂), 56.3 (NCH₂), 123.9 (ArC), 126.0 (ArC), 127.9 (ArC), 133.1 (ArC), 139.4 (ArC), 143.3 (ArC).

1,9-Diethyl Ethylthioninium chloride

N,N-Diethyl-m-ethyl-p-phenylenediamine dihydrochloride (2 g, 7.5 mmol) was dissolved in water (75 cm³) and the solution adjusted to pH 1.6. The pink solution then had sodium sulphide (>60%) (1.35 g, 10.4 mmol) added portionwise. To the suspension was added an aqueous solution of iron (III) chloride (4.22 g, 15.6 mmol in 35 cm³ of water) where there was an immediate colour change to purple. The solution was then aerated for 1 hour before a second portion of iron (III) chloride (4.22 g, 15.6 mmol in 35 cm³ of water) solution was added. The solution was cooled to 5° C. before filtering and washing the precipitate with water. The precipitate was also washed with ethanol and the ethanol concentrated to give a sticky purple solid. To the aqueous filtrate was added sodium chloride (50 g) and the solution was stirred for 10 minutes whereby the colour changed to red/purple as the product was salted out. The suspension was filtered and the solid dissolved in dichloromethane (100 cm³) and methanol (10 cm³) before drying over magnesium sulphate. Filtering and concentration with the ethanol soluble product gave the title compound (0.06 g, 3%) as a purple solid. $\delta_H$ (250 MHz; D₂O): 6.73 (2H, s, ArH), 6.48 (2H, s, ArH), 3.45 (8H, brdq, NCH₂), 2.46 (4H, q, 7.5, CH₂), 1.17 (12H, brdt, CH₃), 0.93 (6H, t, 7.5, CH₃); m/z (ESI) 396.2 (100%, [M-Cl]⁺). Optionally, flash column chromatography was performed to remove iron-chloride residues, with 10% methanol: 90% dichloromethane as eluent and using silica 40-63µ 60 Å.

Synthesis 6

Ethyl-Thioninium Chloride Zinc Chloride Double Salt (ETZ)

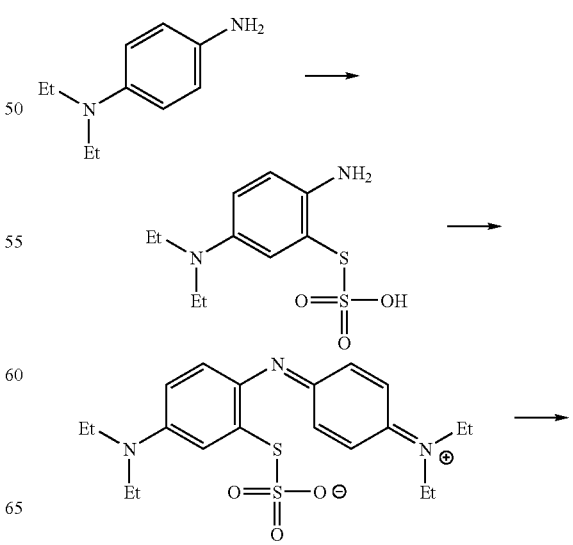

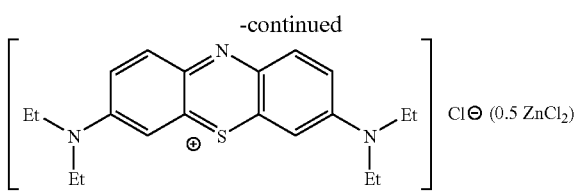

A stirred mixture of N,N-diethyl-p-phenylenediamine (5.0 g, 30.4 mmol) in H$_2$O (100 cm$^3$) and H$_2$SO$_4$ (conc., '98%', 1 cm$^3$) was treated with non-reducing ZnCl$_2$ solution (ZnCl$_2$, 7.60 g, 55 mmol in 15 cm$^3$ of H$_2$O with Na$_2$Cr$_2$O$_7$.2H$_2$O, 100 mg) to produce a reddish reaction mixture. Additions of Al$_2$(SO$_4$)$_{3\text{-}16}$H$_2$O solution (5.80 g, 9.2 mmol in 10 cm$^3$ of H$_2$O), Na$_2$S$_2$O$_3$.5H$_2$O solution (8.0 g, 32.2 mmol in 10 cm$^3$H$_2$O) and one-third of a solution of Na$_2$Cr$_2$O$_7$.2H$_2$O (8.7 g, 29.2 mmol in 15 cm$^3$ of H$_2$O) were followed by a rapid rise in temperature to 40° C. A solution of N,N-diethylaniline (3.0 g, 20.1 mmol in conc. HCl, 4 cm$^3$) was added, and followed by an addition of the remaining Na$_2$Cr$_2$O$_7$.2H$_2$O solution. A dark green precipitate was observed. The temperature was rapidly raised to 75° C., after which a slurry of activated MnO$_2$ (3.80 g, 44.7 mmol in 5 cm$^3$ of H$_2$O) was added. The temperature was raised to 85° C., and left to stir at that temperature for 30 minutes. A blue solution with precipitate was observed. The reaction mixture was cooled to 50° C. and H$_2$SO$_4$ (conc., 11 cm$^3$) was slowly added. The reaction was further cooled to 20° C., and vacuum filtered to recover the precipitate, which was then washed with brine (saturated salt water). This black solid was re-dissolved in H$_2$O (250 cm$^3$) at 100° C., and cooled, followed by vacuum filtration to remove insolubles. The filtrate was treated with ZnCl$_2$ (4 g) and NaCl (23 g) and left in the refrigerator for 16 hours, after which the resulting precipitate was recovered by vacuum filtration, washed with brine (30 cm$^3$), and dried in a vacuum oven for 3 hours, to give the title compound (5.7 g, 71%) as a rusty red powder. δ$_H$ (250 MHz, D$_2$O): 1.20 (12H, br t, CH$_3$), 3.50 (8H, br q, CH$_2$), 6.80 (2H, s, ArH), 7.05 (2H, br d, ArH) and 7.30 (2H, br d, ArH). See, for example, Fierz-David and Blangley, 1949, "F. Oxazine and Thiazine Dyes," in: *Fundamental Processes of Dye Chemistry*, published by Interscience (London, UK), pp. 308-314.

Synthesis 7

Methyl-thioninium Iodide (MTI)

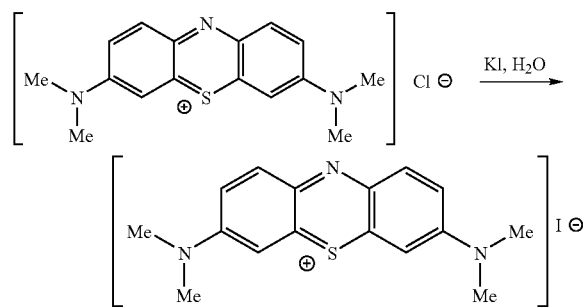

Methyl-thioninium chloride (2.00 g, 6.25 mmol) was dissolved in water (50 cm$^3$) and potassium iodide (1.56 g, 9.4 mmol) was added with stirring. A precipitate formed, which was filtered and the solid was recrystallised from boiling water (50 cm$^3$) to yield the title compound (1.98 g, 77%) as fine green needles. δ$_H$ (250 MHz; DMSO): 7.88 (2H, br d, ArH), 7.49 (4H, br s, ArH), 3.37 (12H, s, CH$_3$). Analysis for C$_{16}$H$_{18}$N$_3$SI: C, 46.72; H, 4.41; N, 10.22; S, 7.80; I, 30, 85. Found: C, 46.30; H, 4.21; N, 10.14; S, 7.86; I, 29.34.

Synthesis 8

Methyl-thioninium Iodide Hydrogen Iodide Mixed Salt (MTI.HI)

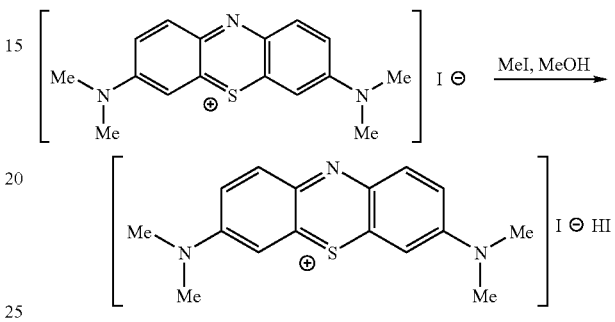

Methyl-thioninium iodide (0.50 g, 1.22 mmol) was dissolved in methanol (20 cm$^3$) and methyl iodide (1.90 g, 13.37 mmol) was added while stirring. The mixture was heated at reflux for 18 hours before additional methyl iodide (0.42 g, 6.69 mmol) was added and the mixture was once again heated to reflux and stirred for 8 hours. The mixture was cooled to room temperature, giving a solid that was filtered and washed with methanol to yield the title compound (0.30 g, 46%) as bronze green solid. δ$_H$ (250 MHz; DMSO): 7.82 (2H, d, J=8.5, ArH), 7.42 (4H, s, ArH), 3.34 (12H, s, CH$_3$). δ$_C$ (62.9 MHz; DMSO): 153.8 (ArC), 137.9 (ArC), 134.9 (ArC), 133.5 (ArC), 119.1 (ArC), 118.8 (ArC), 106.9 (ArC), 106.6 (ArC), 41.1 (NCH$_3$).

Synthesis 9

Ethyl-Thioninium Iodide (ETI)

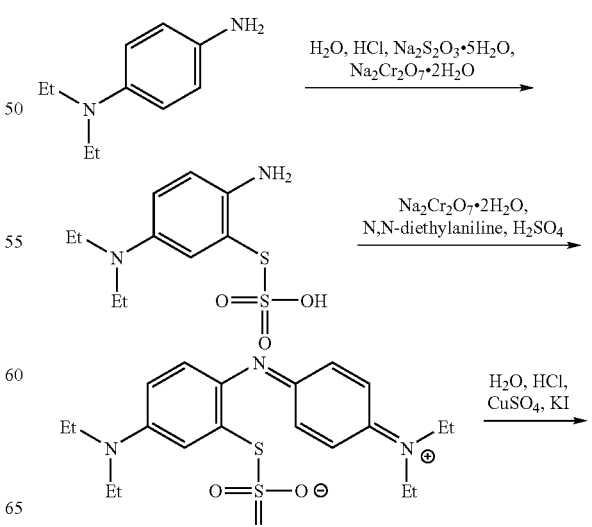

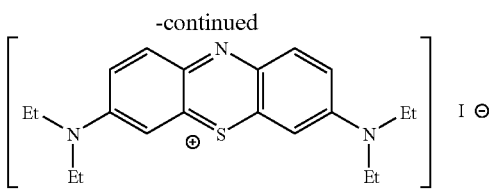

A stirred mixture of N,N-diethyl-p-phenylenediamine (10.0 g, 61 mmol) in aqueous hydrochloric acid (0.5 M, 200 cm$^3$) was adjusted to pH 2 with aqueous sodium hydroxide (10%). The diamine solution was cooled to 5° C. before the addition of aqueous Na$_2$S$_2$O$_3$.5H$_2$O (16.65 g, 67 mmol in 20 cm$^3$H$_2$O). An aqueous solution of Na$_2$Cr$_2$O$_7$.2H$_2$O (7.27 g, 24 mmol in 35 cm$^3$ of H$_2$O) was added dropwise to the mixture over a 15 minute period giving a black suspension. The suspension was stirred at 5° C. for 1 hour (pH=8.07, T=3.7° C.). A solution of N,N-diethylaniline (8.25 g, 61 mmol), H$_2$SO$_4$ (6 g) and water (10 cm$^3$) was cooled to 5° C. before addition to the suspension. An aqueous solution of Na$_2$Cr$_2$O$_7$.2H$_2$O (19.09 g, 64 mmol in 50 cm$^3$ of H$_2$O) was then added dropwise to the mixture over a 20 minute period giving a thick dark green suspension. The mixture was stirred at 5° C. for 2 hours (pH=6.75, T=6° C.) before filtering. The green purple solid obtained was washed with water (2×50 cm$^3$). The solid was slurried in aqueous hydrochloric acid (300 cm$^3$, pH 2) giving a suspension with a pH=6.37 at 22° C. To the suspension was added CuSO$_4$ (1.52 g, 6.1 mmol) and the mixture heated to 90° C. where a deep blue solution formed. After stirring at this temperature for 1 hour the mixture was cooled to 25° C. and filtered. The solid was washed with water (2×50 cm$^3$), the filtrate was adjusted from pH 6.33 to pH 2.00, T=25° C. with hydrochloric acid (5 M). The deep blue solution was heated to 80° C. and potassium iodide (14 g) was added and upon cooling an orange purple precipitate was deposited. Filtration gave a purple powder (8.8 g, 31%), which was recrystallised from hot ethanol (400 cm$^3$) to give the title compound as fine purple needles. Mp 211° C.; ν$_{max}$ (KBr)/cm$^{-1}$: 3574 (CH), 3484 (CH), 3028 (CH), 2965 (CH), 1662 (C=C), 1539 (CH), 1474 (CH), 1346 (CH); δ$_C$ (62.9 MHz, CDCl$_3$): 1.33 (12H, t, 7, CH$_3$), 3.72 (8H, q, 7, NCH$_2$), 7.23 (2H, d, 9.75, ArH), 7.41 (2H, s, ArH), 7.83 (2H, d, 9.75, ArH); δ$_H$ (62.9 MHz, CDCl$_3$):152.4, 138.8, 135.7, 135.2, 118.3, 106.4, 46.8, 13.2.

Synthesis 10

Ethyl-thioninium iodide Hydrogen Iodide Mixed Salt (ETI.HI)

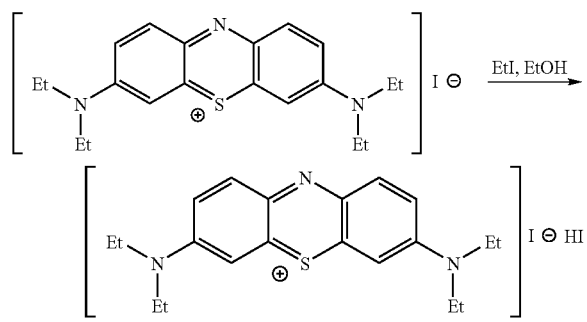

Ethyl-thioninium iodide (2.00 g, 4.28 mmol) was dissolved in ethanol (100 cm$^3$) and ethyl iodide (27.35 g, 175 mmol) was added while stirring. The mixture was heated at reflux for 18 hours, then cooled to room temperature, giving a precipitate that was filtered and washed with ethanol to yield the title compound (1.02 g, 40%) as a bronze solid. δ$_H$ (250 MHz; D$_2$O): 7.90 (2H, br d, ArH), 7.42 (4H, s, ArH), 2.45 (8H, br q, NCH$_2$), 1.23 (12H, br t, CH$_3$).

Synthesis 11

Ethyl-Thioninium Nitrate (ETN)

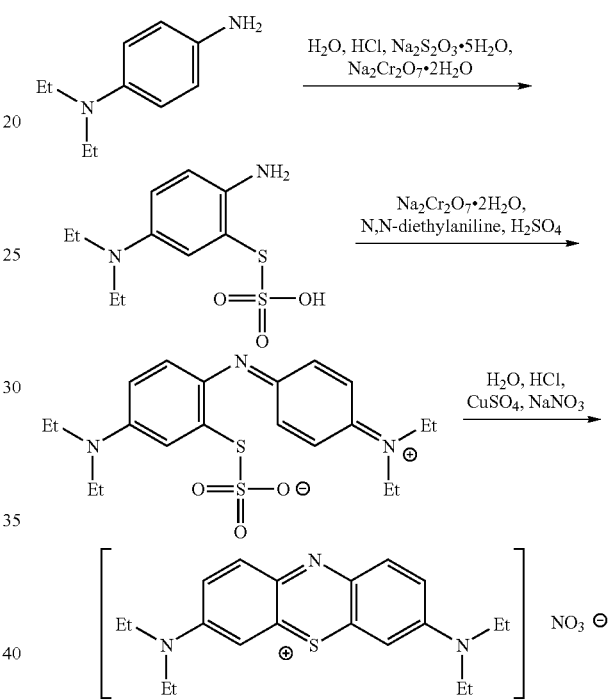

A stirred mixture of N,N-diethyl-p-phenylenediamine (10.0 g, 61 mmol) in aqueous hydrochloric acid (0.5 M, 200 cm$^3$) was adjusted to pH 2 with aqueous sodium hydroxide (10%). The diamine solution was cooled to 5° C. before the addition of aqueous Na$_2$S$_2$O$_3$.5H$_2$O (16.65 g, 67 mmol in 20 cm$^3$H$_2$O). An aqueous solution of Na$_2$Cr$_2$O$_7$.2H$_2$O (7.27 g, 24 mmol in 35 cm$^3$ of H$_2$O) was added dropwise to the mixture over a 15 minute period giving a black suspension. The suspension was stirred at 5° C. for 1 hour (pH=8.07, T=3.7° C.). A solution of N,N-diethylaniline (8.25 g, 61 mmol), H$_2$SO$_4$ (6 g) and water (10 cm$^3$) was cooled to 5° C. before addition to the suspension. An aqueous solution of Na$_2$Cr$_2$O$_7$.2H$_2$O (19.09 g, 64 mmol in 50 cm$^3$ of H$_2$O) was then added dropwise to the mixture over a 20 minute period giving a thick dark green suspension. The mixture was stirred at 5° C. for 2 hours (pH=6.75, T=6° C.) before filtering. The green purple solid obtained was washed with water (2×50 cm$^3$). The solid was slurried in aqueous hydrochloric acid (300 cm$^3$, pH 2) giving a suspension with a pH=6.37 at 22° C. To the suspension was added CuSO$_4$ (1.52 g, 6.1 mmol) and the mixture heated to 90° C. wherein a deep blue solution formed. After stirring at this temperature for 1 hour, the mixture was cooled to 25° C. and filtered. The solid was washed with water (2×50 cm$^3$), the and the filtrate was adjusted from pH 6.33 to pH 2.00, T=25° C. with hydrochloric acid (5 M). The deep blue solution was heated to 80° C. and had sodium nitrate (50 g) added and was allowed to cool to 25° C. slowly while stirring gently. The product was filtered as green needles (6.80 g, 28%). $\delta_H$ (250 MHz, CDCl$_3$): 1.36 (12H, t, 7, CH$_3$), 3.72 (8H, q, 7, NCH$_2$), 7.23 (2H, d, 9.5, ArH), 7.39 (2H, s, ArH), 7.89 (2H, d, 9.5, ArH); $\delta_H$ (62.9 MHz, CDCl$_3$): 152.5, 138.8, 135.7, 135.6, 118.1, 106.4, 46.6, 12.9.

Biological Studies

Methods

Purification of α-Synuclein Proteins

Two plasmids for expression of α-synuclein in *E. coli* were constructed. The core aggregation domain of α-synuclein (amino acids 31-109) was expressed with an N-terminal polyhistidine tag (tsyn), which allows its purification on a Ni-chelating column. Full-length α-synuclein (syn) was expressed without a tag, and purified by ion exchange chromatography on DEAE Sepharose, and in some cases followed by purification on CM-Sepharose. For both proteins, the bacterial extract was first enriched by taking a 30-50% ammonium sulphate cut. The proteins eluted from the column were dialysed against 20 mM CAPS, pH 9.5 or 20 mM Tris.HCl, pH 7.5, 50 mM NaCl (see Table 1 for details), and stored at −70° C.

Fluorescence Assay for Filament Assembly

α-Synuclein proteins (tsyn or fsyn) were incubated at 37° C. for the times indicated in Figure legends with mixing to induce fibril formation. In some cases, 50 µg/ml heparin was included to enhance fibril formation.

Samples of 10 µl were then diluted to 100 µl with water, plus thioflavine T or primulin at 1 µM, or 0.2 or 5 µM in some cases. Fluorescence excitation spectra were measured in 96 well plates in a Varian Carey Eclipse Fluorescence Spectrophotometer, with the emission wavelength at 480 nm. Excitation spectra were corrected for the signal measured without tsyn and the peak signal measured from the spectra. The data were normalised to the value measured without compound and P50 values measured from plots of normalised fluorescence against concentration of compound.

ELISA Assay for Synuclein-Synuclein Binding

A solid phase assay was used to measure self-association of α-synuclein. tsyn diluted in carbonate buffer (pH 8.5) was bound to the assay plate, and full-length α-synuclein (fsyn) was added in the aqueous phase. The aqueous phase binding buffer was 50 mM Na-phosphate, pH 6.0, 20 mM NaCl, 0.05% Tween-20, 1% fish skin gelatine. Bound fsyn was detected using a commercial antibody (211) that does not recognise tsyn.

Example 1

Purification of α-Synuclein

Several different preparations of α-synuclein have been used in the assays described below, and brief details of their purification are summarised in Table 1.

TABLE 1

Purification details of synuclein preparations

| Prep | Purification details |
| --- | --- |
| tsyn-8 | AS cut, Ni column, dialysed 20 mM CAPS, pH 9.5 |
| fsyn-9 | AS cut, DEAE column, dialysed 20 mM Tris, pH 7.5, 50 mM NaCl |
| tsyn-16 | AS cut, Ni column, dialysed 20 mM Tris, pH 7.5 |
| fsyn-10, 17, 18, 19 | AS cut, DEAE column, CM column, dialysed 20 mM Tris•HCl, 50 mM NaCl, pH 7.5 |
| fsyn-14 | AS cut, DEAE column, dialysed 20 mM Tris•HCl, pH 7.5 |
| fsyn-15 | AS cut, DEAE column, SP column, dialysed 20 mM Tris•HCl, pH 7.5 |
| fsyn-20, 22 | AS cut, DEAE column, CM column, dialysed 20 mM CAPS, pH 9.5 |

Protein prepared by heat treatment was inactive in the assay. Protein prepared by DEAE ion-exchange chromatography was active. A further purification step on CM- or SP-Sepharose was therefore carried out. It was found that CM-Sepharose gave the cleanest preparation, but with lower yield than SP-Sepharose. These preparations were compared for binding activity (see Example 9). Table 1 summarises the synuclein preparations used for these experiments.

Example 2

Assay of Synuclein Assembly by Fluorescence

It has been reported that assembly and fibril formation of α-synuclein enhances the fluorescence of thioflavine T. We tested the effect of α-synuclein on the fluorescence of this and also primulin. The proteins were induced to assemble by incubation at 37° C., with and without 50 µg/ml heparin and samples were assayed with 1 µM thioflavine T or primulin at various time points.

Figure 1:
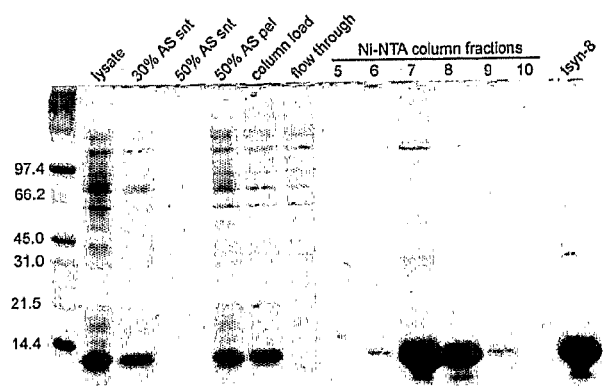
FIG. 1 shows samples from the purification of tsyn analysed by SDS-PAGE and staining with Coomassie Blue. The Ni-affinity column provides a very efficient purification; the final purified protein (tsyn-8 in FIG. 1) is greater than 95% pure, with a yield of 44 mg protein from a 750 ml culture of bacteria.
Figure 2:
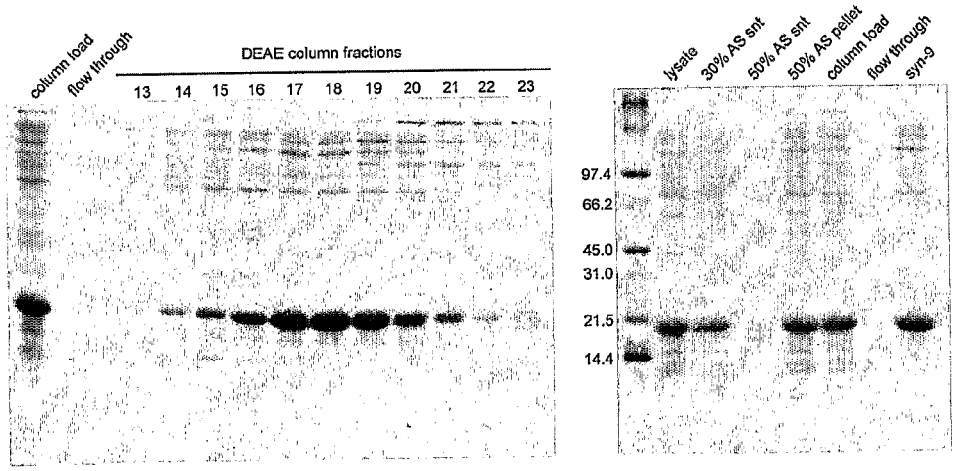
FIG. 2 shows the purification of fsyn on DEAE-Sepharose. The final protein using this method is not so pure (fsyn-9 in FIG. 2).
Figure 3:
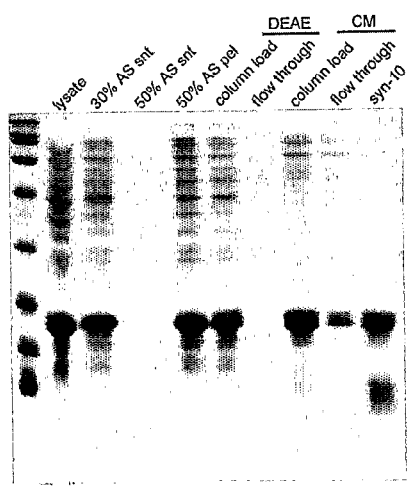
FIG. 3 shows the purification of fsyn on DEAE Sepharose followed by CM-Sepharose. This method produces protein of >95% purity, but the yield is lower (12 mg protein compared to 85 mg with DEAE Sepharose alone).
Figure 4:
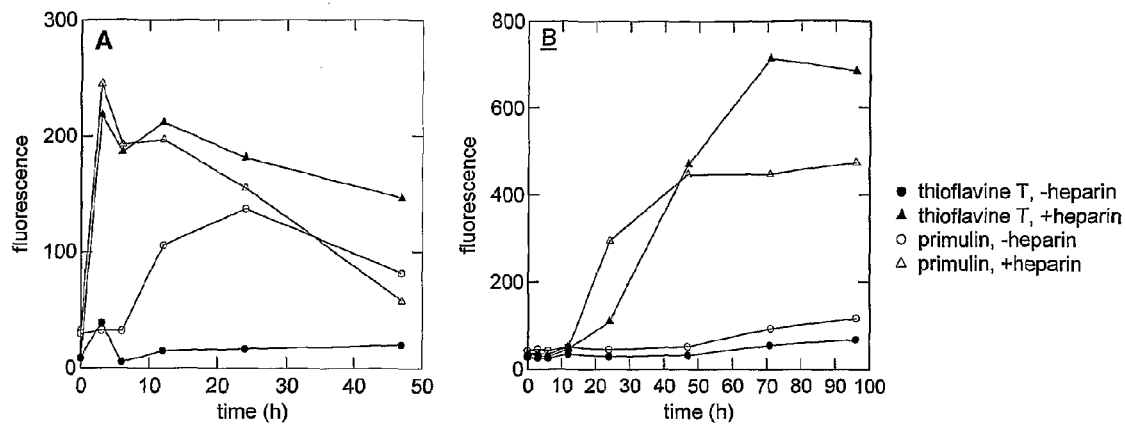

FIG. 4 shows the time course of assembly of tsyn and fsyn preparations. In the absence of heparin, there is very little appearance of thioflavine T fluorescence with either protein (FIG. 4A, 4B). There is appearance of a primulin signal over 20-30 h with tsyn protein in the absence of heparin, in the presence of heparin there is no lag phase for appearance of the primulin signal but the final extent of the fluorescence is similar with and without heparin (FIG. 4A). Heparin stimulates appearance of a thioflavine T signal for tsyn to a similar extent as primulin (FIG. 4A). There is a very slow appearance of both thioflavine T and primulin signals for fsyn in the absence of heparin. In the presence of heparin, there is appearance of a signal with both fluorophores, but with a longer lag phase than seen with tsyn (FIG. 4B). The lag phase for appearance of the primulin signal is shorter than that for thioflavine T, but the final extent of the thioflavine T signal is greater than that for primulin (FIG. 4B). The difference in signal between primulin and thioflavine T indicates that these two fluorophores are detecting different assembly states of synuclein, and is consistent with the idea that primulin detects an early precursor state of assembly prior to fibril formation, which is detected by thioflavine T.

Example 3

Assay of Fibril Disruption by MTC and ETC

The fluorescence effects have been used to assay the effect of compounds MTC and ETC on assembled α-synuclein.

Figure 5:
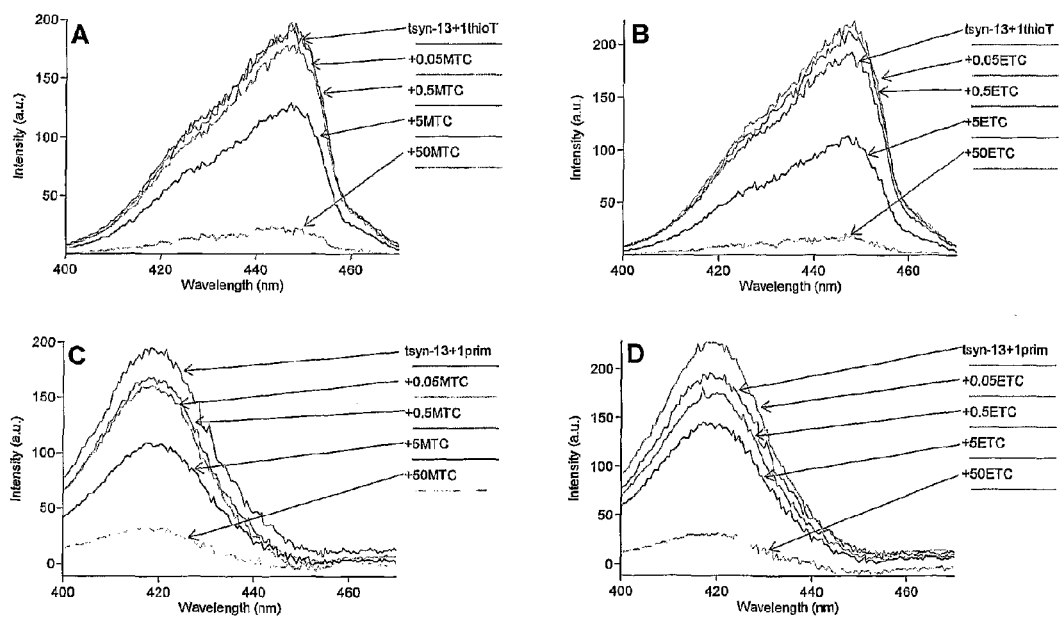
Figure 6:
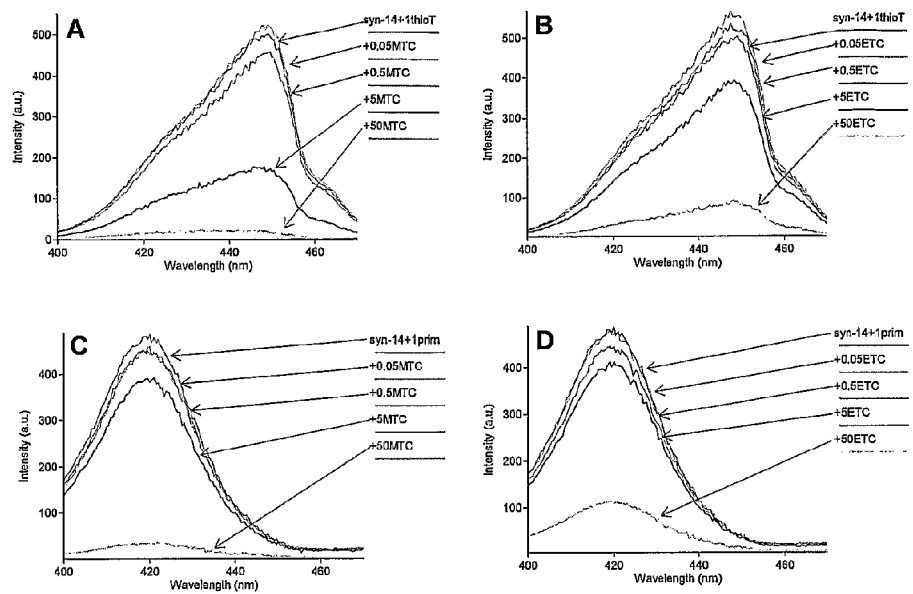
Figure 7:
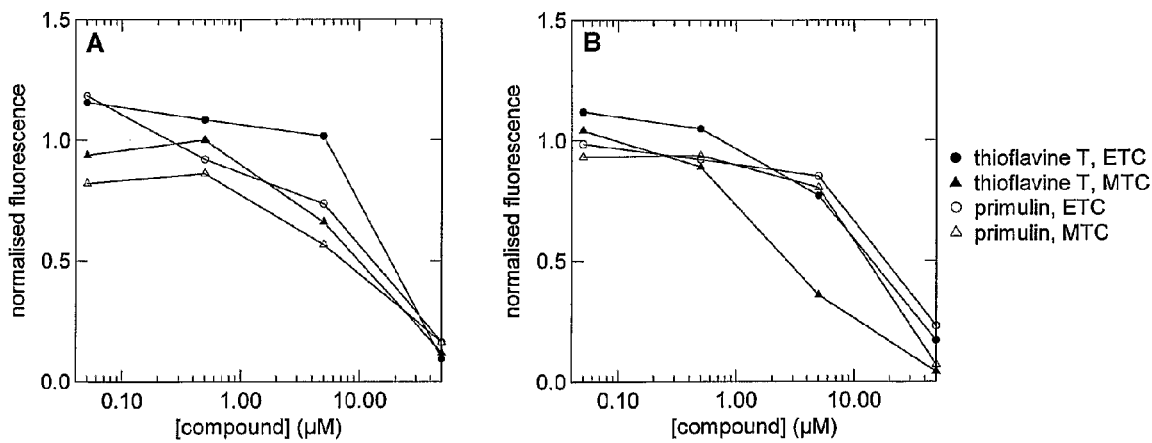

FIG. 5 shows the effect of MTC and ETC on the fluorescence signal of either thioflavine T or primulin induced by assembled tsyn, and the peak fluorescence values from the traces are shown as a function of concentration of compound in FIG. 7A. FIG. 6 shows the effect of MTC and ETC on the fluorescence signal of either thioflavine T or primulin induced by assembled fsyn, and the peak fluorescence values from the traces are shown as a function of concentration of compound in FIG. 7B. The P50 values measured from the graphs in FIG. 7 are summarised in Table 2.

TABLE 2

P50 values for the inhibition of α-synuclein-dependent fluorescence of thioflavine T or primulin by MTC and ETC.

| protein | fluorophore | compound | P50 (µM) |
|---|---|---|---|
| tsyn-13 | thioflavine T | MTC | 18.5 |
| tsyn-13 | thioflavine T | ETC | 30.3 |
| tsyn-13 | primulin | MTC | 12.9 |
| tsyn-13 | primulin | ETC | 24.1 |
| fsyn-14 | thioflavine T | MTC | 3.8 |
| fsyn-14 | thioflavine T | ETC | 25.3 |
| fsyn-14 | primulin | MTC | 23.5 |
| fsyn-14 | primulin | ETC | 30.6 |

Figure 8:
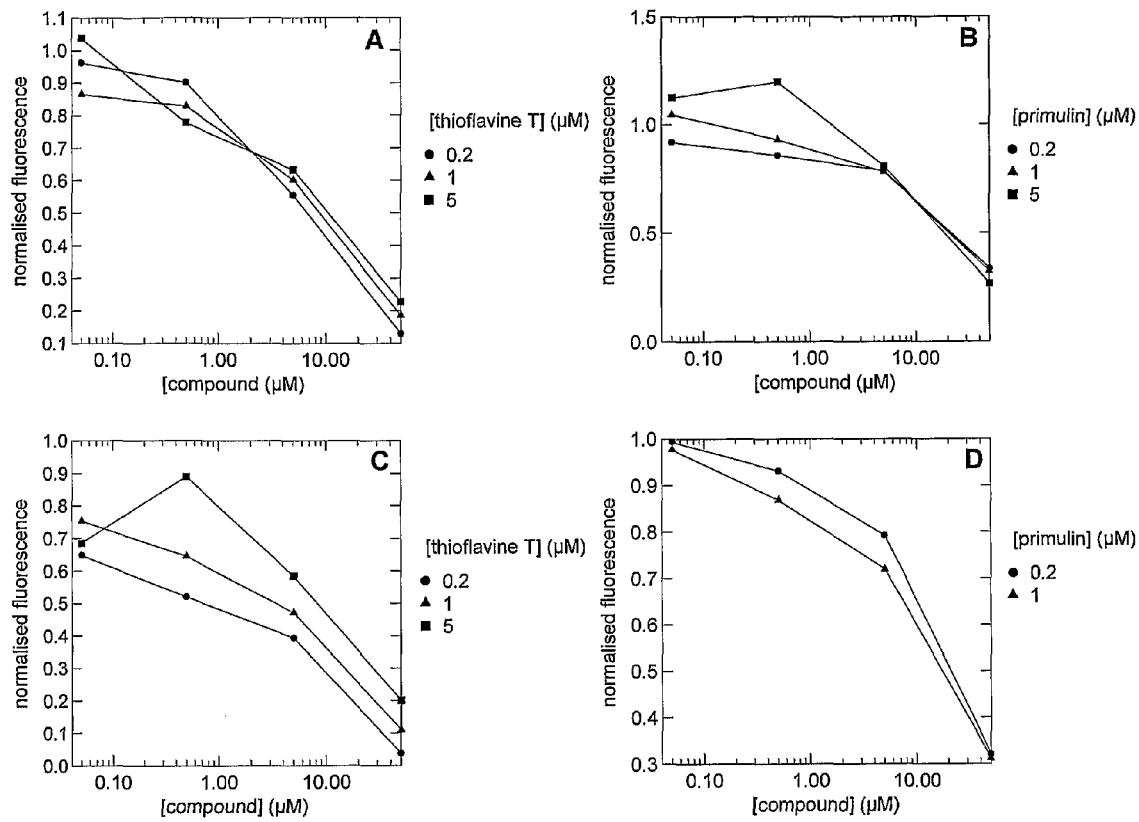

The effect of the compounds on thioflavine T and primulin fluorescence could be due to competition for the fluorescence ligand rather than disruption of the fibrils. To test this, the experiment was done at three different concentrations of fluorophore, since the P50 will be dependent on fluorophore concentration only if the effect is due to competition. Data from one experiment is shown in FIG. 8, and the mean P50s from all experiments is shown in Table 3. There is not a significant difference in P50 values measured over a 25-fold difference in fluorophore concentrations, indicating that the effect of the compounds is due to fibril disruption.

TABLE-3

P50 values for the inhibition of α-synuclein-dependent fluorescence of thioflavine T or primulin by MTC and ETC. Effect of fluorophore concentration.

| compound | fluorophore | [fluorophore] (µM) | P50 (µM) | SEM | N |
|---|---|---|---|---|---|
| MTC | thioflavine T | 0.2 | 11.6 | 6.7 | 3 |
| MTC | thioflavine T | 1.0 | 12.7 | 3.9 | 3 |
| MTC | thioflavine T | 5.0 | 20.2 | 0.0 | 2 |
| MTC | primulin | 0.2 | 41.7 | 8.2 | 2 |
| MTC | primulin | 1.0 | 35.1 | 2.2 | 3 |
| MTC | primulin | 5.0 | 31.2 | 0.7 | 2 |
| ETC | thioflavine T | 0.2 | 3.2 | 2.5 | 3 |
| ETC | thioflavine T | 1.0 | 9.0 | 6.6 | 3 |
| ETC | thioflavine T | 5.0 | 17.6 | 2.3 | 2 |
| ETC | primulin | 0.2 | 41.7 | 8.2 | 2 |
| ETC | primulin | 1.0 | 34.0 | 3.3 | 3 |
| ETC | primulin | 5.0 | 32.3 | — | 1 |

Example 4

The Effect of Compounds on the Assembly of α-Synuclein Aggregates In Vitro

Figure 11:
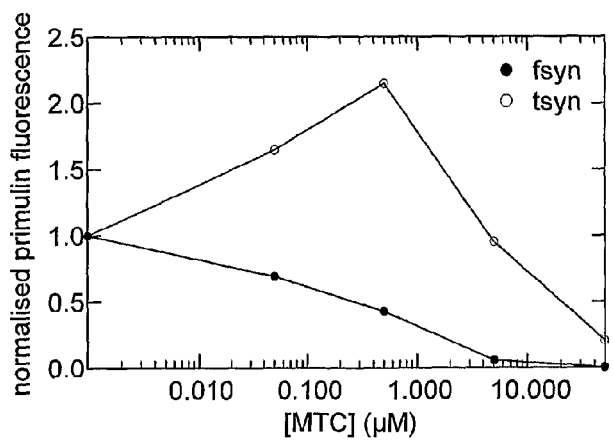

As well as affecting assembled α-synuclein aggregates, MTC also inhibits the assembly of α-synuclein into aggregates, as determined by competition of the binding of primulin. Optimal conditions for the assembly of aggregates from tsyn and fsyn has been determined and the inhibitory effect of MTC is shown in the Figure (New FIG. 11). tsyn (1 mg/ml in 20 mM Tris.HCl, pH 7.5+50 µg/ml heparin) was assembled at 37° C. for 24 hr. MTC inhibits tsyn assembly at concentrations greater than 5) µM (○, open circles). fsyn was assembled under the same conditions, except that the concentration of fsyn was 2 mg/ml and incubation was for 120 hr. MTC shows a greater inhibitory effect with fsyn than with tsyn, with inhibition occurring at 0.05 µM with the former (●, closed circles).

Inhibition of α-synuclein aggregation (fsyn; using the primulin assay as described above) by MTC and ETC was comparable and greater than that observed with DEMTC and DEETC. All these compounds completely inhibited assembly at a concentration of 50 µM.

TABLE 4

Effect of diaminophenothiazines on α-synuclein aggregation using fsyn.

| | Fluorescence with drug concentration (µM): | | | |
|---|---|---|---|---|
| Compound | 0 | 0.5 | 5.0 | 50 |
| MTC | 311.3 | 145.9 | 24.2 | 1.2 |
| ETC | 311.3 | 190.6 | 44.6 | 1.5 |
| DEMTC | 311.3 | 295.7 | 23.4 | 0.0 |
| DEETC | 311.3 | 369.2 | 18.2 | 0.0 |

Figure 12:
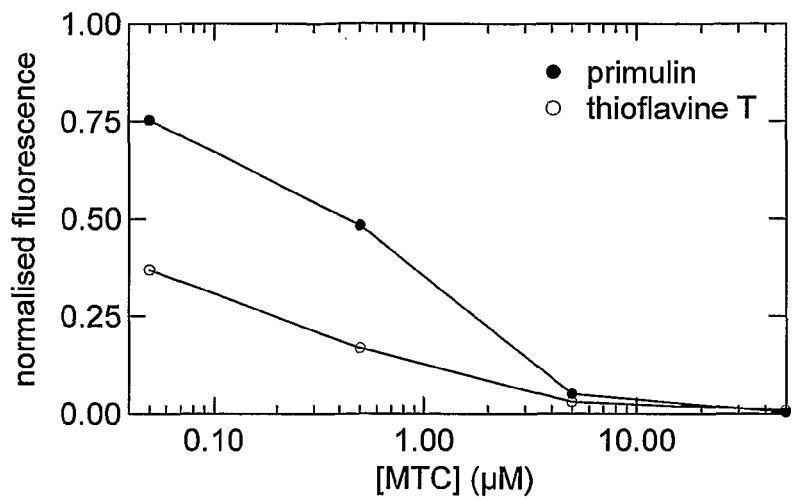

Thioflavine T has also been used to monitor fsyn assembly. The evolution of the thioflavine T signal is slower than the primulin signal, but reaches a higher level and appears to be reporting elongation of fibrils rather than formation of aggregates. At later stages of assembly (160 h) when the thioflavine T signal has reached a plateau, the thioflavine T signal is more sensitive to inhibition by MTC than the primulin signal, with a significant effect being observed at 0.05 µM. This is shown in FIG. 12.

Example 5

Assay of α-Synuclein Binding by a Solid Phase ELISA Assay

The two α-synuclein proteins were also used in a binding assay. The tsyn is bound in the solid phase, and full-length fsyn is added in the aqueous phase. An antibody against a C-terminal epitope in α-synuclein that does not recognise tsyn is used to quantify bound fsyn.

Figure 9:
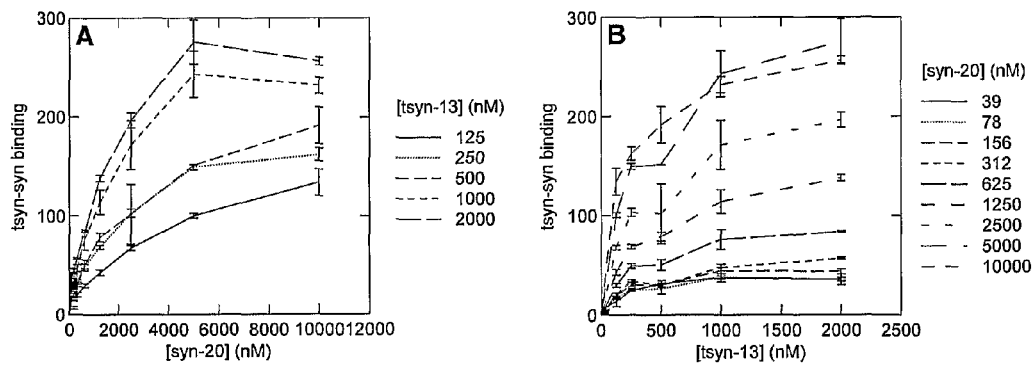

FIG. 9 shows the aqueous and solid phase binding curves for fsyn-20 binding to tsyn-13. Binding of fsyn-20 plateaus at ~5 µM and tsyn-13 binding plateaus at ~2 µM. These concentrations were used to test the effect of various thioninium chlorides and flavones on synuclein-synuclein binding.

Figure 10:
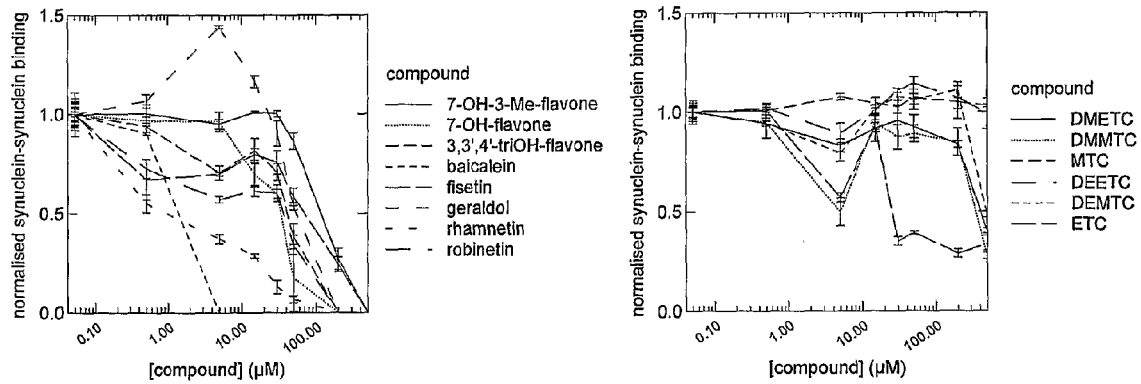

The inhibition curves are shown in FIG. 10, and the B50 values calculated from the curves are summarised in Table 4.

All the flavones tested in the binding assay have good inhibitory activity, whereas although most of the thioninium chlorides are active, namely MTC, ETC, DMMTC, DEMTC, DMETC, DEETC, thionine and tolonium chloride, others such as azure A and azure B are inactive.

TABLE 5

P50 and B50 values for the inhibition of synuclein-synuclein binding.

| Compound | P50 (µM) using thioflavone T | P50 (µM) using primulin | B50 (µM) in α-synuclein binding assay |
|---|---|---|---|
| MTC | 15.4 ± 3.7 (6) | 30.4 ± 3.0 (6) | 130.8 ± 15.0 (5) |
| ETC | 7.3 ± 3.8 (5) | 26.0 ± 6.0 (5) | 3.8 ± 0.3 (2) |
| DMMTC | 0.2 (1) | 20.7 ± 7.8 (2) | 4.9 (1) |
| DEMTC | | | 0.8 ± 0.4 (2) |
| DMETC | 0.9 ± 0.2 (2) | 5.0 ± 0.9 (3) | 0.5 ± 0.1 (2) |
| DEETC | | | 0.4 (1) |
| Azure A | 3.8 ± 0.9 (2) | 17.9 ± 2.0 (2) | >500 |
| Azure B | | | >500 |
| Thionine | 3.8 ± 0.3 (5) | 23.0 ± 2.2 (5) | 32.2 ± 11.7 (2) |
| Tolonium chloride | 1.5 ± 0.2 (5) | 8.8 ± 3.3 (5) | 3.3 ± 0.3 (2) |
| Baicalein | 47.6 | 28.2 | 2.5 (1) |
| 7-Hydroxy-flavone | >50 | >50 | 35.3 (1) |
| 7-hydroxy-3-methyl-flavone | | | 141.2 (1) |
| Fisetin | | | 88.2 (1) |
| Geraldol | >50 | >50 | 60.8 (1) |
| Rhamnetin | 39.4 | 34.7 | 11.4 ± 9.7 (2) |
| Robinetin | 21.1 | 27.6 | 39.2 (1) |
| 3,3',4'-Trihydroxy-flavone | | | 43.1 (1) |
| Primulin | | (1.0) | |
| Thioflavine T | (1.0) | | |

P50 measured with 1 µg/ml tsyn-16 assembled in 20 µM Tris•HCl (pH 7.5) with heparin (50 µg/ml) and assayed with either of two fluorophores (1 µM), thioflavine T or primulin. B50 measured with 1 µM tsyn-16 (solid phase) and 5 µM fsyn-20 (aqueous phase), using 50 mM sodium phosphate buffer (pH 6.0) containing 20 mM NaCl.

Example 6

Cell Based Assay for α-Synuclein Aggregation

The cell based assay employed a mouse neuroblastoma cell line NIE-115 that had been engineered to express full-length α-synuclein incorporating an N-terminal signal sequence (SSfsyn) to target incorporation of the protein into the membrane (see WO02/059150). When the cells were differentiated with dibutyryl cyclicAMP (dbcAMP) (1 mM) expression of the α-synuclein protein was increased.

α-synuclein protein was detected by immunoblot using various anti-α-synuclein antibodies. These included: mAb 42 (BD Biosciences Cat No. 610787) that recognises an epitope within tsyn (residues 31-109 of α-synuclein). In addition to α-synuclein, mAb 42 also reacts non-specifically with a protein of higher molecular mass (the protein is not recognised by other anti-α-synuclein antibodies). This protein was used as an estimate of cell numbers as the level of this protein in cells correlates with cell density. Drugs were tested with these cells and an inhibitory activity (EC50) was calculated by determining the drug concentration in which the ratio of α-synuclein to the non-specific band fell to 50% of the value for cells treated with dbcAMP alone.

Figure 13:
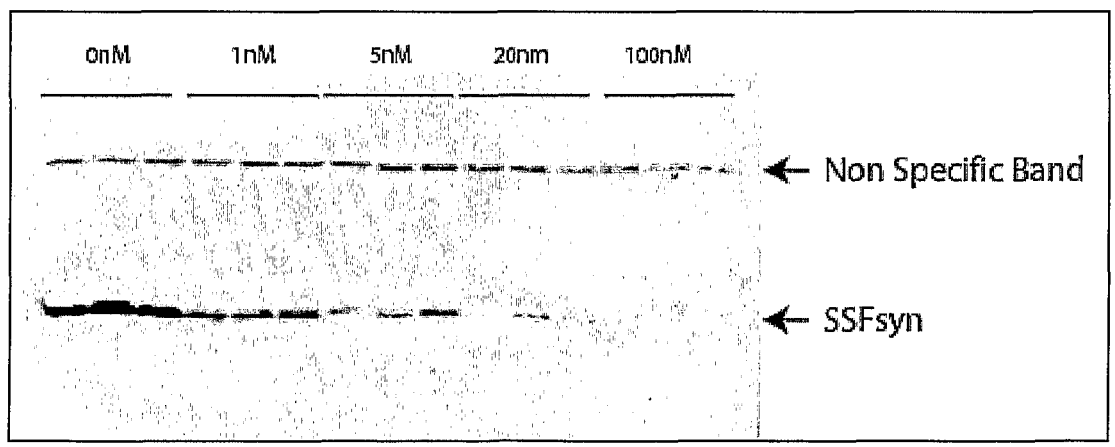

The timing of the addition of the dbcAMP and drug was varied and the length of time that the cells are left in the presence of drug+dbcAMP before collecting cells was also be varied. A typical result is shown in FIG. 13 for DEETC.

MTC was inhibitory when the cells had been left for more than 2 days in the presence of MTC and dbcAMP. The most effective compound was DEETC that inhibited in the nM range; DEMTC, DMETC and ETC also show inhibitory activity (Table 6). The flavone, rhamnetin, was also inhibitory.

TABLE 6

Inhibition of FSyn expression in NIE cells differentiated with dbcAMP by phenothiazine compounds.

| Compound | EC50 (µM) | LD50 (µM) |
|---|---|---|
| MTC | 1.17 ± 0.3 (7) | 62 |
| ETC | 0.08 ± 0.02 (13) | 38 |
| DMMTC | 0.10 ± 0.02 (4) | 1.2 |
| DMETC | 0.05 ± 0.04 (2) | 6 |
| DEMTC | 0.012 ± 0.005 (3) | 3 |
| DEETC | 0.004 ± 0.001 (3) | 1.0 |
| Tolonium chloride | 0.26 ± 0.05 (3) | 1.2 |
| Azure A | 0.32 | 8.8 |
| Azure B | 0.25 | 0.8 |
| Rhamnetin | 2.5 | 31 |

Example 7

Truncation and Aggregation of α-Synuclein in a Cell-Based Assay

Figure 14:
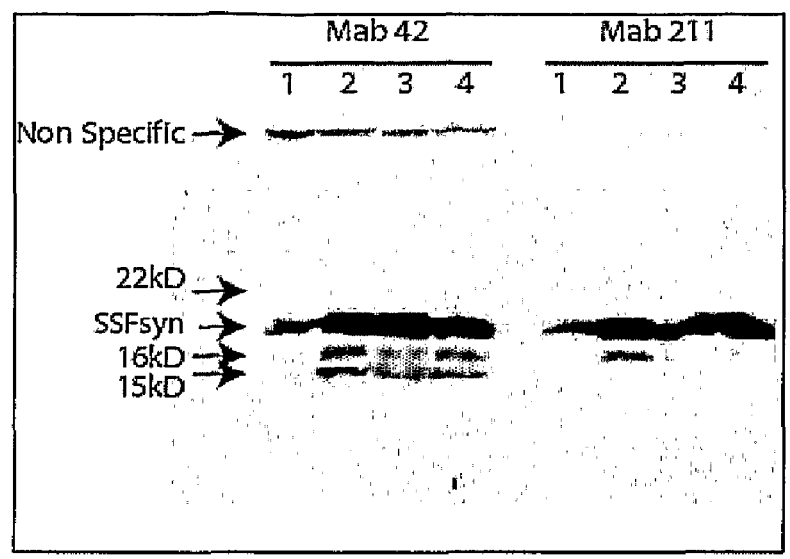

When DH60.21 NIE cells were differentiated using dbcAMP, there was increased expression of SSFsyn, as detected using mAb 42 (recognising the core of α-synuclein) or mAb 211 (recognising a C-terminal epitope of α-synuclein). In addition, two lower molecular mass bands of approximately 15 and 16 kDa were produced. The latter may correspond to Fsyn lacking the signal sequence. While the larger of these two proteins was detected by both of these antibodies, the 15 kDa band was, at best, only weakly detected using mAb 211. A typical example is shown in FIG. 14. This suggests that this is a protein that has been C-terminally truncated. A further 22 kDa band with an apparent mobility greater than FSyn was also observed, but only using mAb 42 and not mAb 211 (FIG. 14). The ratio of the 22-kDa to SSFsyn bands differed significantly depending upon the antibody used (p<0.001; Table 7). This suggests the presence of aggregated synuclein that has been truncated at both N- and C-termini. This 22-kDa band was also observed in SH-SY5Y neuroblastoma cells transfected with SSFsyn.

TABLE 7

Presence of aggregated and truncated α-synuclein in cells as demonstrated by the absence of reactivity with the C-terminal mAb 211.

| Detection antibody | Mean ratio of 22 kDa:SSFsyn (±SEM; n = 30) |
|---|---|
| mAb 42 | 0.14 ± 0.02 |
| mAb 211 | 0.01 ± 0.003 |

Figure 15:
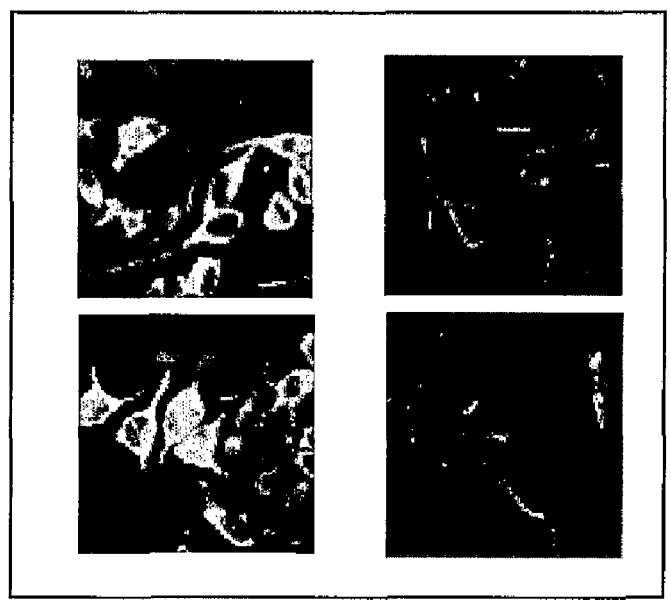
Figure 16:
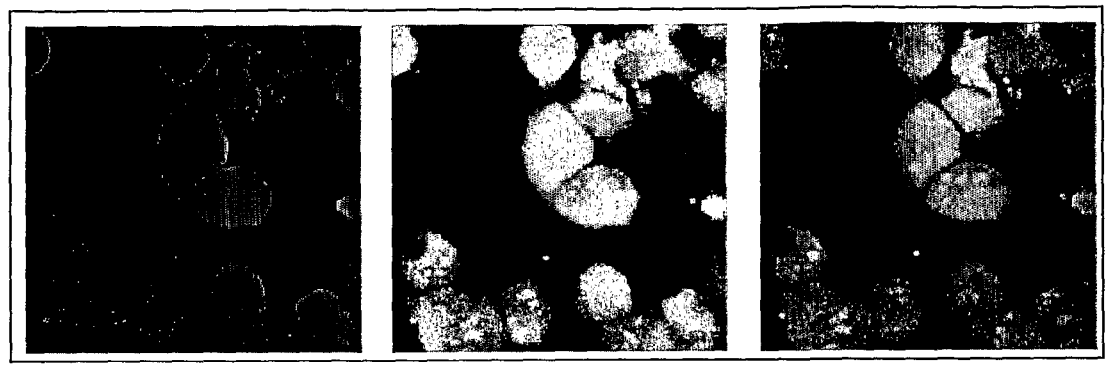

When cells expressing SSFsyn were examined by fluorescence microscopy, abundant expression was observed, including material of a granular nature, suggestive of aggregated protein (FIG. 15). Furthermore the aggregates observed in cells were simultaneously recognised by primulin, a fluorophore that binds to aggregated proteins (FIG. 16). This confirms other studies that demonstrate that α-synuclein aggregation arises after differentiation of SH-SY5Y neuroblastoma cells (Hasegawa et al. 2004; Brain Res. 1013:51-59)

Example 8

Effect of MTC on α-Synuclein Oligomer Assembly and on α-Synuclein Binding of In Vitro Referring to the results of P50 and B50 measurements in synuclein assays in Table 5, it can be seen that thioninium chlorides generally have lower P50s than flavones in the synuclein assays, although some of the flavones have low B50s, comparable to the thioninium chlorides. This suggests that although both classes of compound are effective in inhibiting the synuclein self aggregation reaction, only thioninium chlorides have the ability to disrupt preformed aggregates.

Figure 17:
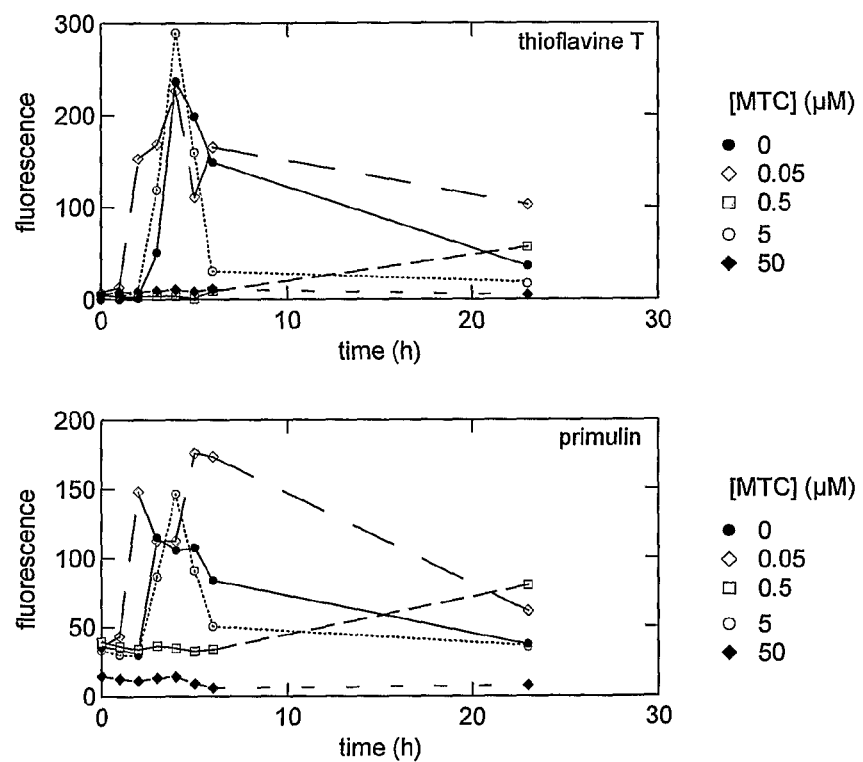

As a further assay of the activity of MTC, its effect was measured over the time course of assembly of tsyn (FIG. 17). As shown in FIG. 17, in the absence of MTC, there is a lag phase before assembly of ~2 hours. The fluorescence signal peaks at 4-5 hours, then gradually decreases over 20 hours. The time course of appearance of fluorescence is similar for the two fluorophores. In the presence of a low concentration of MTC (0.05 μM), the lag phase before start of assembly is reduced to 1 hour and the final fluorescence signal after 24 hours is higher. In particular, with primulin, the maximum fluorescence is higher with primulin compared to thioflavine T. In the presence of 0.5 μM MTC, assembly is slower than control, but the final fluorescence level is higher than control. At 5 μM MTC, the time course for assembly over the first 4-5 hours is similar to the control, but then there is a more rapid fall off in the fluorescence, although the final fluorescence level is similar to control. At 50 μM MTC, there is no assembly over the time course of the experiment. The data in FIG. 17 show that MTC has a complex effect on the assembly of synuclein; at low concentrations (molar ratio synuclein:MTC 2000:1) MTC apparently stimulates assembly to some degree, whereas at higher concentrations (maximum molar ratio of synuclein:MTC 2:1), it completely inhibits assembly. Without wishing to be bound by theory, it is surmised that MTC provides a ligand cross-linking effect at a low molar ratio that is insufficient to allow inhibition of aggregation but allows binding of the compound to more than one synuclein molecule to promote aggregation.

Example 9

Optimisation of the α-Synuclein Solid Phase Binding Assay

Figure 18:
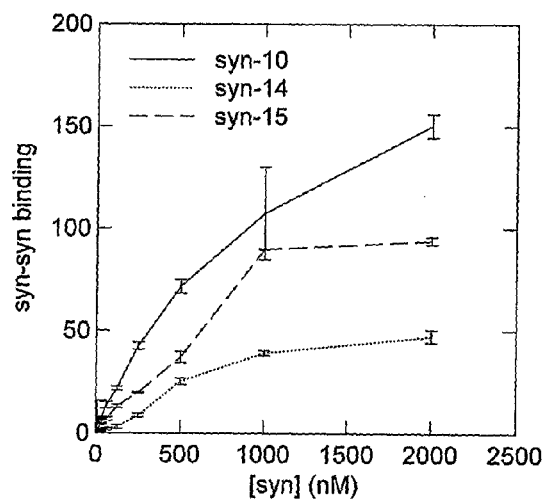

FIG. 18 shows the binding curves for three different synuclein preparations, as described in Example 1. The best binding was shown using syn-10, which was the most pure preparation, and the worst binding using syn-14, which was the least pure. This suggests that the second purification step removes a contaminant that inhibits binding, and that the protein should be purified with a second CM-Sepharose step, even thought this reduces the yield.

Syn-10 gave the best binding of the three preparations tested, but the maximum extent of binding is still quite low. Two different solid phase preparations of tsyn were tested and showed no difference, and the concentration of tsyn used was shown to be optimal (data not shown). Different buffer conditions for the aqueous phase step were therefore tested.

Figure 19:
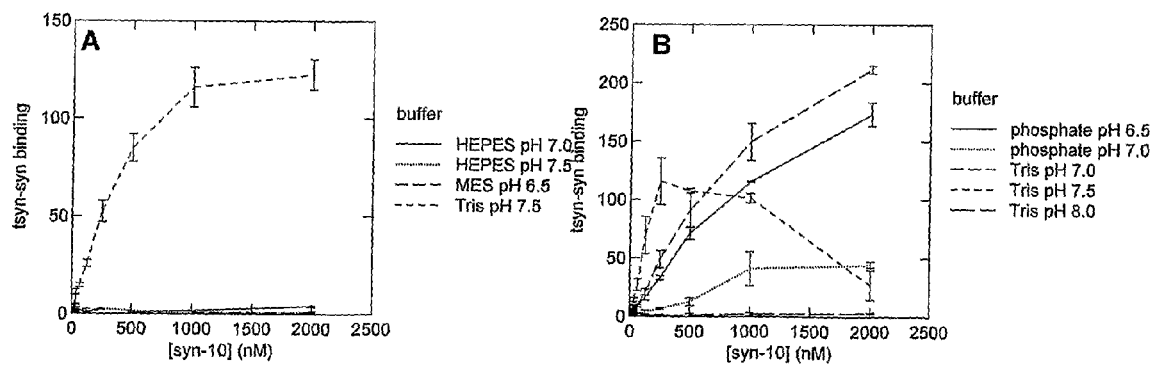

FIG. 19A shows that the buffers, HEPES and MES, completely abolished binding of syn. FIG. 19B shows that Tris buffer at pH 7.0 allowed better binding than the pH 7.5 used previously. Tris at pH 8.0 gave worse binding, so a lower pH appeared to be better for syn binding. Since Tris cannot be used to buffer at lower pHs, phosphate buffer was also tried, to allow testing at pH 6.5. Phosphate at pH 6.5 gave better binding than phosphate at pH 7.0. Notwithstanding the variation in binding between the experiments, these results show that the chemical nature of the buffer, as well as the pH, influences binding of syn, and that the best buffer was Tris, pH 7.0.

Figure 20:
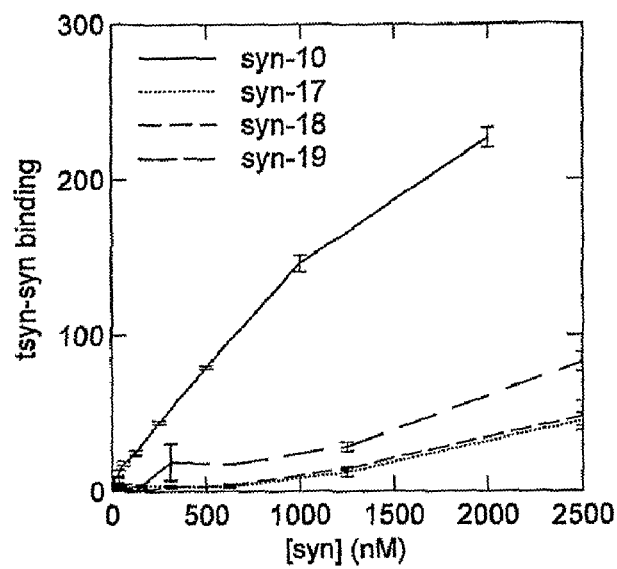
Figure 21:
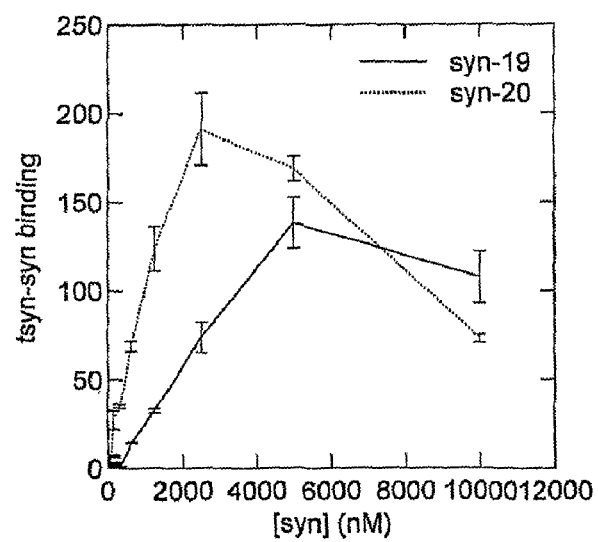

The data in FIG. 18 show that the best purification method for syn for solid phase binding assays is DEAE-followed by CM-chromatography. Three more preparations of syn, purified in this way, were also tested in Tris (pH 7.0) buffer (FIG. 20). The results demonstrate that there is some variability in the binding characteristics between preparations. In a further method, the protein was dialysed against a high pH buffer (syn-20). The binding of this protein is compared with syn-19 in FIG. 21. The fall off in binding after 2 μM is due to a high non-specific binding, the value of which is subtracted from the binding. Syn-20 showed significantly better binding than syn-19, validating the change of dialysis buffer.

Figure 22:
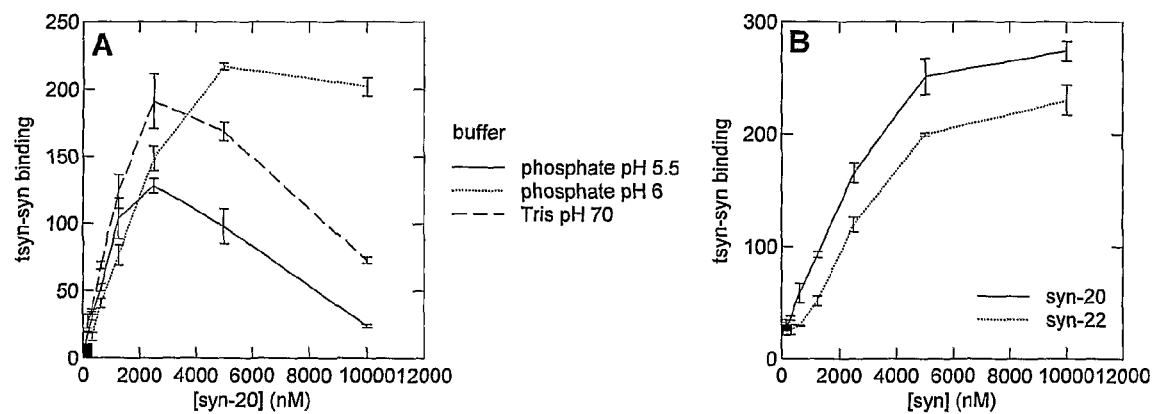

In order to try and reduce variability, the use of phosphate buffer at lower pH values was also investigated. FIG. 22A shows that fsyn-20 assayed in phosphate buffer at pH 6.0 gives better binding than Tris at pH 7.0 or phosphate at pH 5.5. Importantly, there is no fall off of the curve at higher fsyn concentration due to increased background. A second fsyn preparation (fsyn-22) also dialysed against high pH CAPS was tested in phosphate buffer at pH 6.0 and gave similar binding to fsyn-20 (FIG. 22B). Fsyn prepared with a final high pH dialysis and assayed in phosphate buffer at pH 6.0 was used for solid phase inhibition assays (Example 5).

REFERENCES

Galvin, J. E., Uryu, K., Lee, V. M., and Trojanowski, J. Q. (1999) Axon pathology in Parkinson's disease and Lewy body dementia hippocampus contains α-, β-, and γ-synuclein, Proc. Natl. Acad. Sci. U.S.A. 96, 13450-13455.

Uversky, V. N., Li, J., Souillac, P. O., Millett, I. S., Doniach, S., Jakes, R., Goedert, M., and Fink, A. L. (2002) Biophysical properties of the synucleins and their propensities to fibrillate: Inhibition of α-synuclein assembly by β- and γ-synucleins, J. Biol. Chem. 277, 11970-11978.

Park, J. Y., and Lansbury, P. T., Jr. (2003) β-Synuclein inhibits formation of αi-synuclein protofibrils: A possible therapeutic strategy against Parkinson's disease, Biochemistry 42, 3696-3700.

Hashimoto, M., Rockenstein, E., Mante, M., Mallory, M., and Masliah, E. (2001) β-Synuclein inhibits α-synuclein aggregation: A possible role as an anti-parkinsonian factor, Neuron 32, 213-223.

The invention claimed is:

1. A method of treatment of a synucleinopathy, which synucleinopathy results in a neurodegenerative disease state and/or clinical dementia,
   which method comprises orally administering to a subject a therapeutically effective amount of a diaminophenothiazine compound having the following formula:

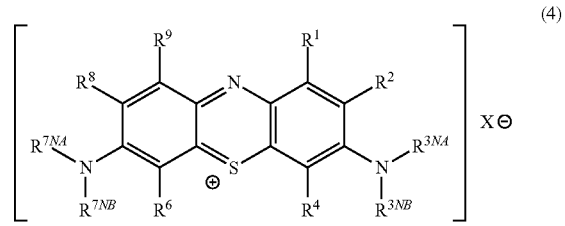

(4)

wherein each one of $R^1$, $R^2$, $R^4$, $R^6$, $R^8$, and $R^9$ is independently selected from:
—H;
—F; —Cl; —Br; —I;
—OH; —OR;

—SH; —SR;
—NO$_2$;
—C(=O)R;
—C(=O)OH; —C(=O)OR;
—C(=O)NH$_2$; —C(=O)NHR; —C(=O)NR$_2$; —C(=O)NR$^{N1}$R$^{N2}$;
—NH$_2$; —NHR; —NR$_2$; —NR$^{N1}$R$^{N2}$;
—NHC(=O)H; —NRC(=O)H; —NHC(=O)R; —NRC(=O)R; and
—R;

wherein each R is independently selected from:
unsubstituted aliphatic C$_{1-6}$alkyl; substituted aliphatic C$_{1-6}$alkyl;
unsubstituted aliphatic C$_{2-6}$alkenyl; substituted aliphatic C$_{2-6}$alkenyl;
unsubstituted C$_{3-6}$cycloalkyl; substituted C$_{3-6}$cycloalkyl;
unsubstituted C$_{6-10}$-carboaryl; substituted C$_{6-10}$carboaryl;
unsubstituted C$_{5-10}$heteroaryl; substituted C$_{5-10}$heteroaryl; and
unsubstituted C$_{6-10}$-carboaryl-C$_{1-4}$alkyl; substituted C$_{6-10}$-carboaryl-C$_{1-4}$alkyl;
wherein, in each group —NR$^{N1}$R$^{N2}$, independently, R$^{N1}$ and R$^{N2}$ taken together with the nitrogen atom to which they are attached form a ring having from 3 to 7 ring atoms;
each one of R$^{3NA}$ and R$^{3NB}$ is independently selected from:
—H;
unsubstituted aliphatic C$_{1-6}$alkyl; substituted aliphatic C$_{1-6}$alkyl;
unsubstituted aliphatic C$_{2-6}$alkenyl; substituted aliphatic C$_{2-6}$alkenyl;
unsubstituted C$_{3-6}$cycloalkyl; substituted C$_{3-6}$cycloalkyl;
unsubstituted C$_{6-10}$-carboaryl; substituted C$_{6-10}$-carboaryl;
unsubstituted C$_{5-10}$heteroaryl; substituted C$_{5-10}$heteroaryl; and
unsubstituted C$_{6-10}$-carboaryl-C$_{1-4}$alkyl; substituted C$_{6-10}$-carboaryl-C$_{1-4}$alkyl;
or: R$^{3NA}$ and R$^{3NB}$ taken together with the nitrogen atom to which they are attached form a ring having from 3 to 7 ring atoms;
and wherein the group —NR$^{7NA}$R$^{7NB}$ is the same as the group —NR$^{3NA}$R$^{3NB}$:
and wherein X is one or more anionic counter ions to achieve electrical neutrality;
and pharmaceutically acceptable salts, mixed salts, and hydrates-thereof;
wherein the therapeutically effective amount of a diaminophenothizine compound orally administered to the subject is selected from the group consisting of
(i) a daily total dose of the diaminophenothizine compound orally administered to the subject of 200 mg-400 mg;
(ii) a daily total dose of the diaminophenothizine compound orally administered to the subject of 100 mg-400 mg;
(iii) in dosage units of about 10, 20, 30, 40, 50, 60, 80, 90, 100, 110, 120, or 130 mg three times a day; and
(iv) in dosage units of about 10, 20, 30, 40, 50, 60, 80, 90, 100, 110, 120, 130, 140, 150, 160, 170, 180, 190, or 200 mg twice a day.

2. The method according to claim 1, wherein each one of R$^1$, R$^2$, R$^4$, R$^6$, R$^8$, and R$^9$ is independently selected from: —H and —R.

3. The method according to claim 1, wherein each one of R$^1$, R$^2$, R$^4$, R$^6$, R$^8$, and R$^9$ is independently selected from: —H, -Me, -Et, -nPr, and -iPr.

4. The method according to claim 1, wherein each of R$^1$, R$^2$, R$^4$, R$^6$, R$^8$, and R$^9$ is —H.

5. The method according to claim 1, wherein each one of R$^{3NA}$ and R$^{3NB}$ is independently selected from: —H, -Me, -Et, -nPr, and -iPr.

6. The method according to claim 5, wherein each one of R$^{3NA}$ and R$^{3NB}$ is independently selected from: —H and -Me.

7. The method according to claim 1, wherein X$^-$ is selected from Cl$^-$, Br$^-$, and I$^-$.

8. The method according to claim 1, wherein the compound is selected from the following compounds, and pharmaceutically acceptable salts, mixed salts, and hydrates thereof:

A  MTC

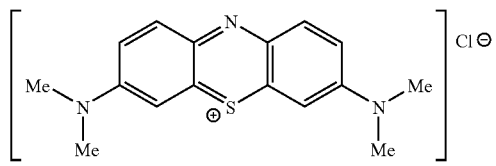

methyl-thionininium chloride

B  ETC

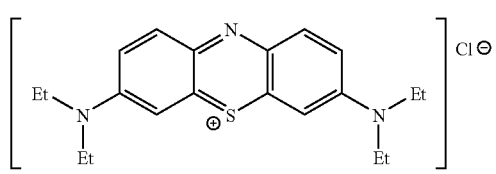

ethyl-thionininium chloride

-continued
C  DMMTC  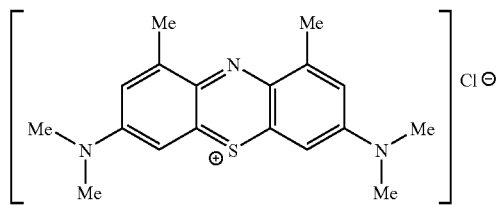
1,9-dimethyl-methyl-thionininium chloride
D  DEMTC  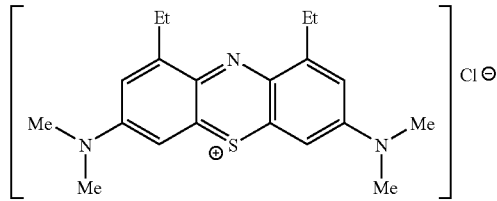
1,9-diethyl-methyl-thionininium chloride
E  DMETC  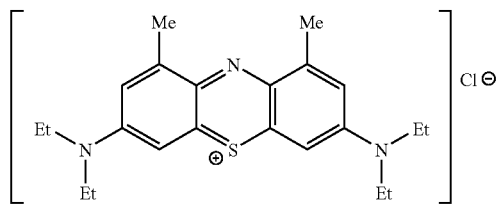
1,9-dimethyl-ethyl-thionininium chloride
F  DEETC  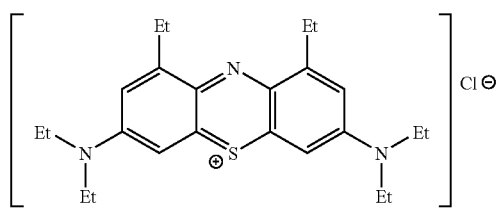
1,9-diethyl-ethyl-thionininium chloride
G  MTZ  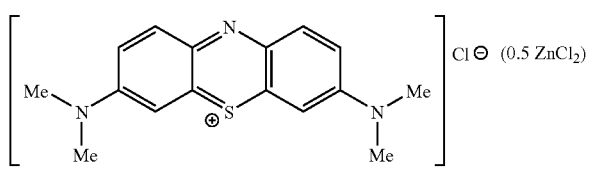
methyl-thionininium chloride zinc chloride mixed salt
H  ETZ  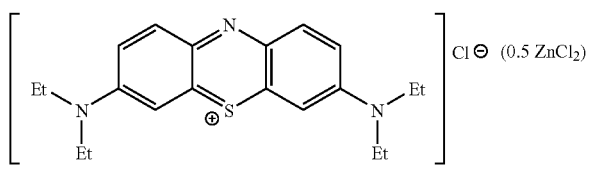
ethyl-thionininium chloride zinc chloride mixed salt

| | | |
|---|---|---|
| I | MTI | 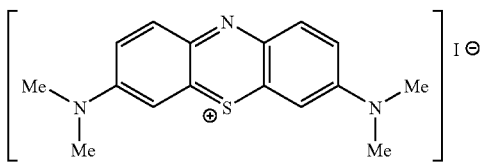<br>methyl-thionininium iodide |
| J | MTI.HI | 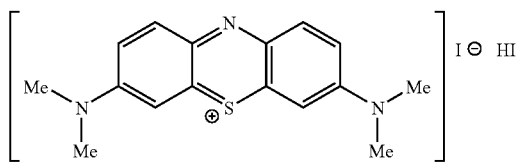<br>methyl-thionininium iodide hydrogen iodide mixed salt |
| K | ETI | 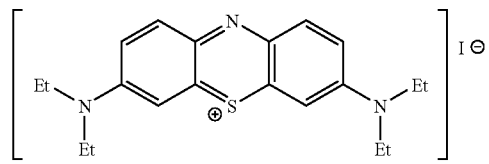<br>ethyl-thionininium iodide |
| L | ETI.HI | 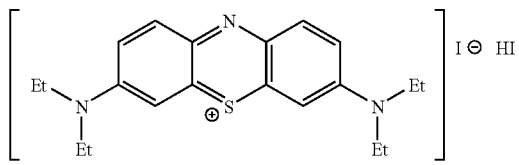<br>ethyl-thionininium iodide hydrogen iodide mixed salt |
| M | MTN | 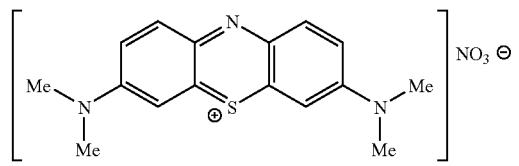<br>methyl-thionininium nitrate |
| N | ETN | 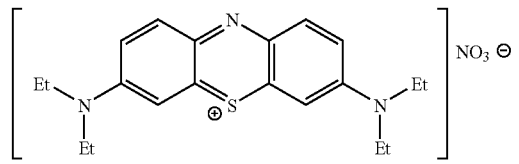<br>ethyl-thionininium nitrate |

9. The method according to claim 1 wherein said treatment comprises orally administering to said subject said diaminophenothizine compound in combination with a compound that modulates dopamine levels in the subject.

10. The method according to claim 1 wherein a 400, 300, 200, or 100 mg daily total dose of said diaminophenothizine compound is orally administered to the subject.

11. The method according to claim 1 wherein the synuclein is α-synuclein.

12. The method according to claim 1, wherein a daily total dose of the diaminophenothizine compound orally administered to the subject is 200 mg-400 mg.

13. The method according to claim 1, wherein a daily total dose of the diaminophenothizine compound orally administered to the subject is 100 mg-400 mg.

14. The method according to claim 1 wherein the subject is orally administered the diaminophenothiazine compound in dosage units of about 10, 20, 30, 40, 50, 60, 80, 90, 100, 110, 120, or 130 mg three times a day.

15. The method according to claim 1, wherein the subject is orally administered the diaminophenothiazine compound in dosage units of about 10, 20, 30, 40, 50, 60, 80, 90, 100, 110, 120, 130, 140, 150, 160, 170, 180, 190, or 200 mg twice a day.

* * * * *